US012616816B2

(12) United States Patent
    Leeflang et al.

(10) Patent No.:    US 12,616,816 B2
(45) **Date of Patent:        *May 5, 2026**

(54) CATHETER DEVICES AND METHODS FOR MAKING THEM

(71) Applicant: CLPH, LLC, Palo Alto, CA (US)

(72) Inventors: Stephen Arie Leeflang, Sandy, UT (US); Christian Scott Eversull, Palo Alto, CA (US)

(73) Assignee: CLPH, LLC, West Valley City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/395,230

(22) Filed: Dec. 22, 2023

(65) Prior Publication Data

US 2024/0238557 A1        Jul. 18, 2024

Related U.S. Application Data

(63) Continuation of application No. 16/915,947, filed on Jun. 29, 2020, now Pat. No. 11,850,375, which is a continuation of application No. 16/186,436, filed on Nov. 9, 2018, now Pat. No. 10,695,532, which is a continuation of application No. 15/464,360, filed on Mar. 21, 2017, now Pat. No. 10,124,145, which is a
(Continued)

(51) Int. Cl.
    *A61M 25/00*        (2006.01)
    *A61M 25/01*        (2006.01)
(52) U.S. Cl.
    CPC .... *A61M 25/0053* (2013.01); *A61M 25/0026* (2013.01); *A61M 25/0028* (2013.01); *A61M 25/0029* (2013.01); *A61M 25/0045* (2013.01); *A61M 25/005* (2013.01); *A61M 25/0136*

(2013.01); *A61M 25/0147* (2013.01); *A61M 2025/0047* (2013.01); *A61M 2025/0166* (2013.01)

(58) Field of Classification Search
    CPC .......... A61M 25/0053; A61M 25/0026; A61M 25/0028; A61M 25/0029; A61M 25/005; A61M 25/0136; A61M 25/0147; A61M 2025/0047; A61M 2025/0166
    See application file for complete search history.

(56) References Cited

U.S. PATENT DOCUMENTS

| | | | | |
|---|---|---|---|---|
| 10,124,145 B2 * | 11/2018 | Leeflang | .......... | A61M 25/0026 |
| 11,850,375 B2 * | 12/2023 | Leeflang | .......... | A61M 25/0029 |

* cited by examiner

*Primary Examiner* — Tasnim Mehjabin Ahmed
(74) *Attorney, Agent, or Firm* — William A. English; Vista IP Law Group LLP

(57)        ABSTRACT

Catheters, sheaths, or other tubular devices are provided that include a proximal end, a distal end sized for introduction into a patient's body, and a steerable distal portion. The tubular device includes a primary lumen extending between the proximal and distal ends; an auxiliary lumen adjacent the primary lumen; and one or more reinforcement members including windings extending helically along at least the distal portion, at least some of the windings passing between the primary and steering element lumens and at least some of the windings surrounding both the primary and steering element lumens. In one embodiment, a steering element is slidably disposed within the auxiliary lumen. Apparatus and methods for making such tubular devices are also provided.

20 Claims, 10 Drawing Sheets

Related U.S. Application Data continuation of application No. PCT/US2015/051284, filed on Sep. 21, 2015.

(60) Provisional application No. 62/053,188, filed on Sep. 21, 2014.

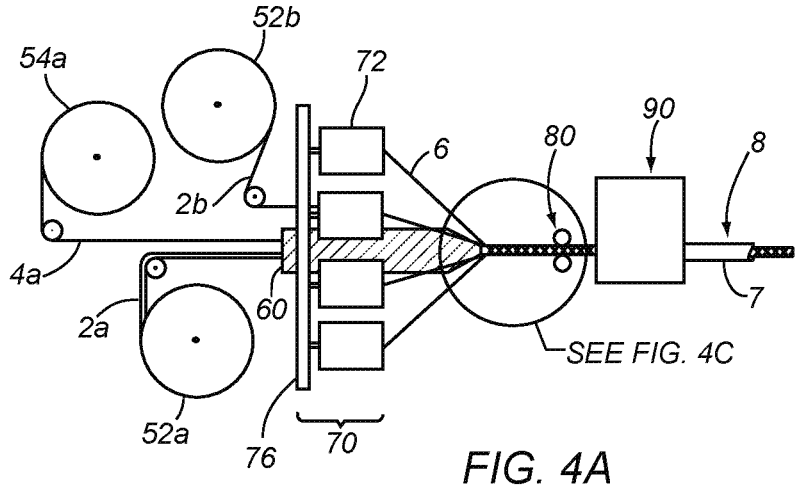
FIG. 4A
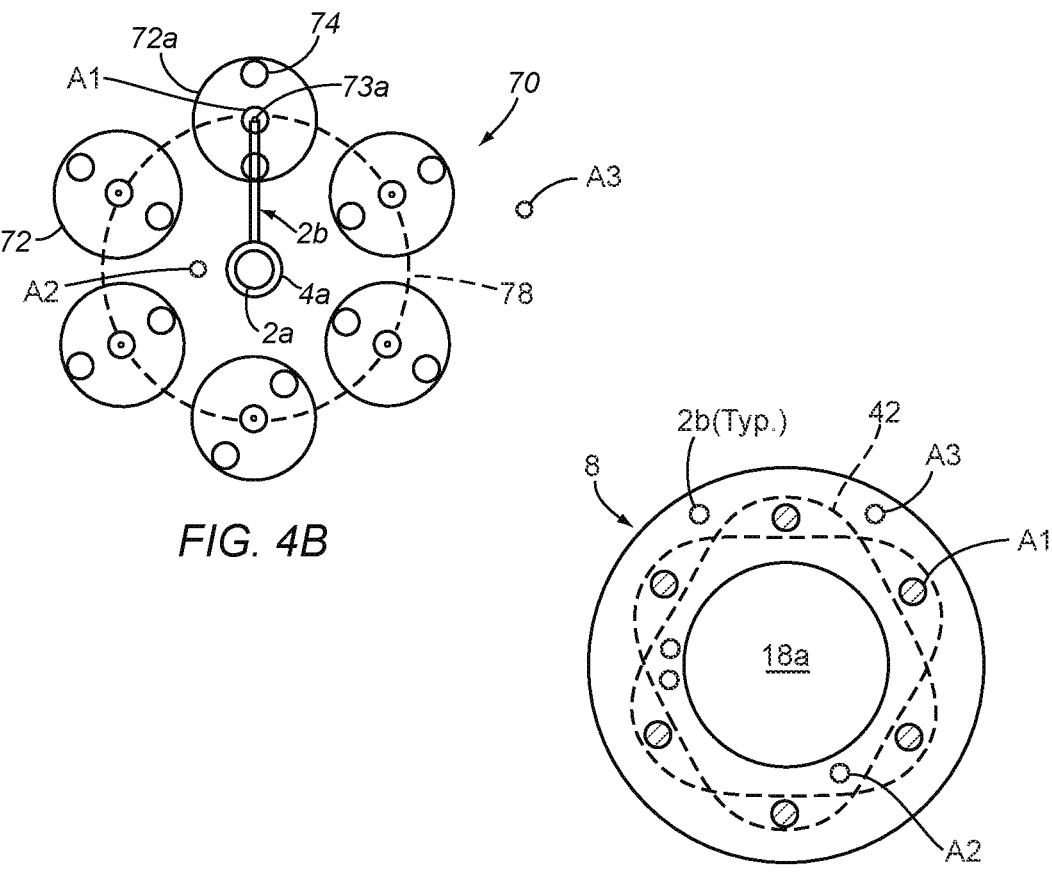
FIG. 4B
FIG. 4C

652 - JACKET STOP/SHIM

LAMINATE
& REMOVE JACKET STOP

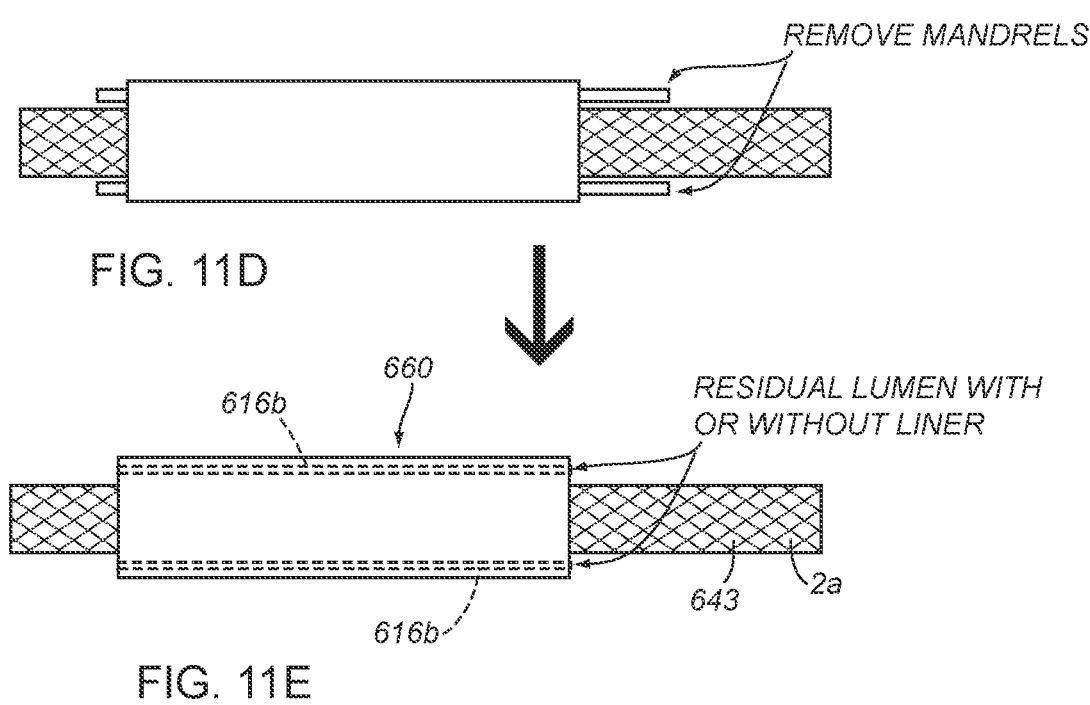
REMOVE MANDRELS
FIG. 11D
RESIDUAL LUMEN WITH
OR WITHOUT LINER
FIG. 11E
ADD PULL WIRE & TRIM BRAID
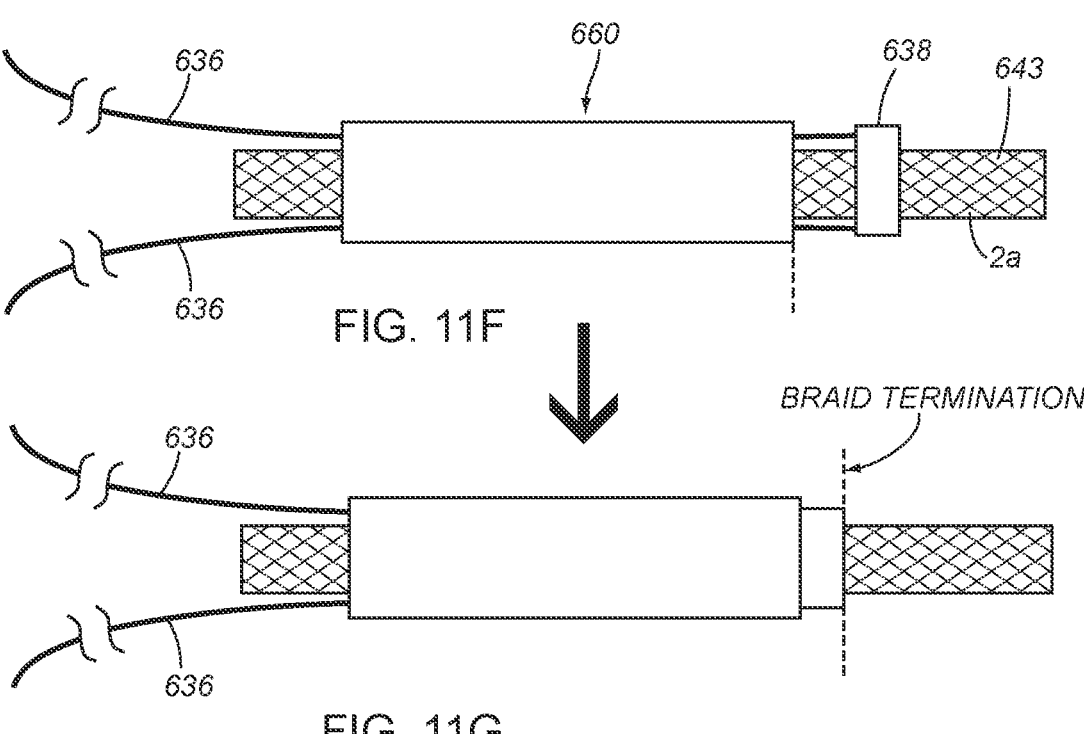
FIG. 11F
BRAID TERMINATION
FIG. 11G

*LAMINATE, TRIM, FORM, REMOVE INNER MANDREL*

616

610

612

614

CATHETER DEVICES AND METHODS FOR MAKING THEM

RELATED APPLICATION DATA

This application is a continuation of co-pending application Ser. No. 16/915,947, filed Jun. 29, 2020, issuing as U.S. Pat. No. 11,850,375, which is a continuation of Ser. No. 16/186,436, filed Nov. 9, 2018, now U.S. Pat. No. 10,695, 532, which is a continuation of application Ser. No. 15/464, 360, filed Mar. 21, 2017, now U.S. Pat. No. 10,124,145, which is a continuation of International Application No. PCT/US2015/051284, filed Sep. 21, 2015, which claims benefit of provisional application Ser. No. 62/053,188, filed Sep. 21, 2014, the entire disclosures of which are expressly incorporated by reference herein.

FIELD OF THE INVENTION

The present invention relates generally to reinforced catheters, sheaths, or other tubular devices including multiple lumens, and, more particularly, to catheters, sheaths, or other tubular devices including braided or other reinforcement configurations and one or more lumens that change position relative to the reinforcement members and/or a central lumen along the length of the tubular devices, and to methods for making such tubular devices.

BACKGROUND

Elongate tubular devices, such as diagnostic or treatment catheters or sheaths may be provided for introduction into a patient's body, e.g., the patient's vasculature or other body lumens. For example, a catheter may have a distal portion configured to be introduced into a body lumen and advanced to one or more desired locations within the patient's body by manipulating a proximal end of the catheter.

To facilitate introduction of such a catheter, one or more wires, cables, or other steering elements may be provided within the catheter, e.g., that are coupled to the distal portion and may be pulled or advanced from the proximal end to deflect the distal portion. For example, a steering element may be provided that is intended to deflect the distal portion within a predetermined plane and/or into a desired curved shape.

Pull wires are a common way to impart deflection ability to such a catheter. However, there are a number of drawbacks associated with such pull wires. For example, a pull wire occupies a significant amount of space within the catheter body. In addition, a pull wire frequently needs to be reinforced, e.g., on the inside and outside of the braid or other reinforcement of the catheter, e.g., to prevent "pull through" or loosening when the pull wire is actuated by pushing or pulling, i.e., the resulting bending moment may cause the pull wire to separate layers of or tear at least partially through the wall of catheter, potentially splitting the catheter and/or decreasing the mechanical actuation ability of the pull wire. Further, a pull wire can make the torque properties of the catheter non-homogenous, making it difficult or impossible to torque the catheter when the pull wire is actuated, e.g., within a tortuous pathway. Further, auxiliary lumens, in particular those located in the wall of a large bore sheath, are difficult to manufacture with consistency due to difficulties with alignment, hand assembly, and the like.

Accordingly, there is a need for improved catheters, sheaths, and other tubular devices and methods of their manufacture.

SUMMARY

The present invention is directed to reinforced catheters, sheaths, or other tubular devices including multiple lumens. More particularly, the present invention is directed to catheters, sheaths, or other tubular devices, e.g., steerable tubular devices, including braided or other reinforcement configurations and one or more lumens that change position relative to the reinforcement members and/or a central lumen along the length of the tubular devices, and/or to methods for making such catheters, sheaths, or other tubular devices.

In accordance with one embodiment, a tubular device is provided, e.g., for a catheter or sheath, comprising a proximal end and a distal end sized for introduction into a patient's body. The tubular device may include a central lumen extending between the proximal and distal ends; an auxiliary lumen extending between the proximal and distal ends adjacent the central lumen; and one or more reinforcement members including windings extending around the central lumen between the proximal and distal ends. In addition, one or more layers may surround the one or more reinforcement members and/or the lumens. At one or more locations along the length of the tubular device, the auxiliary lumen may change position relative to the reinforcement members, e.g., may be at least partially braided, woven, or directed into the reinforcement members, between the reinforcement members and the central lumen, and outside the reinforcement members along different portions of the tubular device.

In accordance with yet another embodiment, a method is provided for making a tubular body that includes directing a primary mandrel along a central axis of a braiding apparatus such that the primary mandrel is surrounded by a plurality of horn gears and/or bobbin carriers or other reinforcement carrying elements; and directing a secondary mandrel adjacent to the primary mandrel and offset from the central axis. One or more reinforcement members from the reinforcement carrying elements may be wrapped around the primary mandrel, and an outer jacket may be applied around the primary and secondary mandrels after wrapping the one or more reinforcement members.

Along a first portion of the primary mandrel, the reinforcement members may be directed such that some windings of the reinforcement members surround the primary mandrel and pass between the primary mandrel and the secondary mandrel, and some windings of the reinforcement members surround both the primary and secondary mandrels. Along a second portion of the primary mandrel, all of the windings of the reinforcement members may surround both the primary mandrel and the secondary mandrel. Optionally, along a third portion of the primary mandrel, the reinforcement members may be wrapped around the primary mandrel such that the secondary mandrel is outside the reinforcement members.

Alternatively, along a first portion of the primary mandrel, all of the windings of the reinforcement members may surround both the primary mandrel and the secondary mandrel, and along a second portion, the reinforcement members may be directed such that some windings of the reinforcement members surround the primary mandrel and pass between the primary mandrel and the secondary mandrel, and some windings of the reinforcement members surround both the primary and secondary mandrels. Optionally, along a third portion of the primary mandrel, the reinforcement members may be wrapped around the primary mandrel such that the secondary mandrel is outside the reinforcement members.

In another alternative, along a first portion of the primary mandrel, the reinforcement members may be wrapped around the primary mandrel such that the secondary mandrel is outside the reinforcement members, and along a second portion of the primary mandrel, all of the windings of the reinforcement members may surround both the primary mandrel and the secondary mandrel or the reinforcement members may be wrapped around the primary mandrel such that the secondary mandrel is outside the reinforcement members The primary mandrel may be removed to define a primary lumen within the tubular body. In addition, the method may also include removing the secondary mandrel to define an auxiliary lumen within the tubular body adjacent the primary lumen. As a result, the position of the auxiliary lumen, e.g., radially and/or circumferentially relative to the primary lumen, may change along the length of the tubular body, e.g., between the first, second, and/or optionally third portions.

In accordance with another embodiment, a method is provided for making a tubular body that includes directing a primary mandrel along a central axis of a braiding apparatus such that the primary mandrel is surrounded by a plurality of reinforcement carrying elements; providing a plurality of reinforcement carrying elements in a predetermined configuration relative to the central axis; providing a source of a secondary mandrel at a first location adjacent to the primary mandrel and offset from the central axis; with the secondary mandrel feeding from the source at the first location, wrapping reinforcement members from the reinforcement carrying elements helically around a first portion of the primary mandrel such that some windings of the one or more reinforcement members surround the primary mandrel and pass between the primary mandrel and the secondary mandrel and some windings of the one or more reinforcement members surround both the primary and secondary mandrels; moving the source of secondary mandrel to a second location; with the secondary mandrel feeding from the source at the second location, wrapping reinforcement members from the reinforcement carrying elements helically around a second portion of the primary mandrel such that either a) all of the reinforcement members also surround the secondary mandrel; or b) the second secondary mandrel remains outside the reinforcement members. An outer jacket may be applied around the primary and secondary mandrels after wrapping the one or more reinforcement members therearound; and the primary mandrel may be removed to define a primary lumen within the tubular body.

In accordance with still another embodiment, a method is provided for making a tubular body using a braiding apparatus comprising a primary mandrel source configured to direct a primary mandrel along a central axis, a plurality of horn gears rotatably mounted around the central axis in a predetermined arrangement such that the horn gears rotate about respective horn gear axes and carriers travel along a generally circular path around the central axis during operation of the braiding apparatus, and a secondary mandrel source configured to direct a secondary mandrel towards the primary mandrel from one of a plurality of locations comprising a first location disposed adjacent the central axis within the generally circular path, a second location aligned with a horn axis of one of the horn gears, and a third location outside the generally circular path. The method may include braiding a first portion of the primary mandrel by: a) directing the primary mandrel along the central axis; b) directing the secondary mandrel from one of the plurality of locations towards the primary mandrel such that the secondary mandrel is disposed adjacent the first portion of the mandrel; and c) wrapping reinforcement members from the carriers around the first portion of the primary mandrel. The method may also include braiding a second portion of the primary mandrel by: a) moving the secondary mandrel source another of the plurality of locations; b) directing the primary mandrel further along the central axis; and c) wrapping reinforcement members from the carriers around the second portion of the primary mandrel. An outer jacket may be applied around the first and second portions of the primary mandrel and the secondary mandrel, and the primary mandrel may be removed to define a primary lumen within the tubular body.

In accordance with yet another embodiment, a tubular device is provided for a catheter or sheath comprising a proximal end and a distal end sized for introduction into a patient's body that includes a central lumen extending between the proximal and distal ends; an auxiliary lumen extending at least partially between the proximal and distal ends adjacent the central lumen; one or more reinforcement members comprising windings extending helically around the central lumen between the proximal and distal ends; and one or more layers surrounding the one or more reinforcement members, wherein the tubular device comprises a first portion in which at least some of the windings pass between the central and auxiliary lumens and at least some of the windings surround both the central and auxiliary lumens, and a second portion in which either a) all of the windings surround both the central and auxiliary lumens or b) all of the windings surround the central lumen and the auxiliary lumen is disposed outside the windings.

In accordance with still another embodiment, an apparatus is provided for performing a procedure within a patient's body that includes a tubular member comprising a proximal end, a distal end sized for introduction into a patient's body, a central axis extending therebetween, and a distal portion extending distally from an intermediate portion to the distal end; a primary lumen extending between the proximal and distal ends and surrounding at least a portion of the central axis; a steering element lumen extending at least partially between the proximal and distal ends adjacent the primary lumen; a steering element slidably disposed within the steering element lumen and comprising a distal end fixed to the tubular member distal end and a proximal end adjacent the proximal end of the tubular member; and an actuator on the proximal end coupled to the steering element proximal end such that, actuation of the actuator applies axial tension or compression to the steering element, thereby causing the distal portion to bend. One or more reinforcement members comprising windings may extend around the primary lumen between the proximal and distal ends, and one or more layers may surround the one or more reinforcement members, wherein the tubular member comprises a first portion in which at least some of the windings pass between the primary lumen and the steering element lumen and at least some of the windings surrounding both the primary lumen and the steering element lumen, and a second portion in which either a) all of the windings surround both the primary lumen and the steering element lumen or b) all of the windings surround the primary lumen and the steering element lumen is disposed outside the windings.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 4A is a schematic of an exemplary embodiment of a braiding apparatus for making a reinforced tubular member including multiple mandrels supported by reinforcement members.

FIG. 4B is a front view of an arrangement of horn gears for creating a braided configuration of reinforcement members that may be included in the braiding apparatus of FIG. 4A and including various locations for sources of mandrels.

FIG. 4C is a cross-sectional view of a catheter showing the locations of mandrels corresponding to the different locations for the sources of mandrels shown in FIG. 4B.

FIGS. 11A-11J show an exemplary method for making a steerable catheter including a lapped braid with a pull wire ring.

DETAILED DESCRIPTION OF THE EXEMPLARY EMBODIMENTS

Figure 1A:
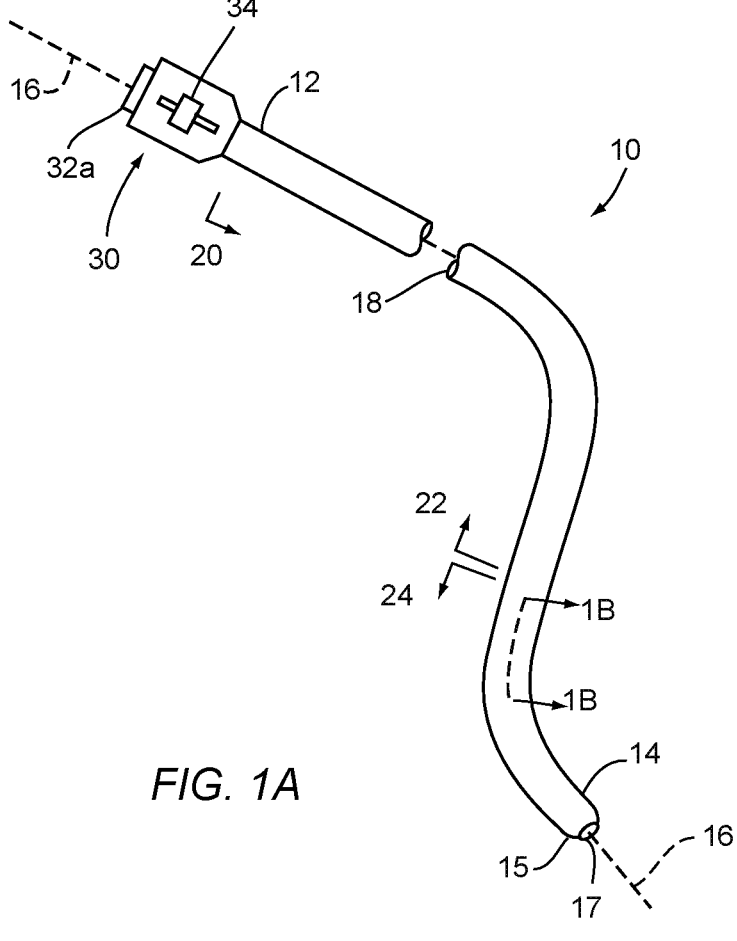
FIG. 1A is a perspective view of an exemplary embodiment of a catheter, including multiple lumens extending between proximal and distal ends thereof, and including a steerable distal portion.
Figure 1B:
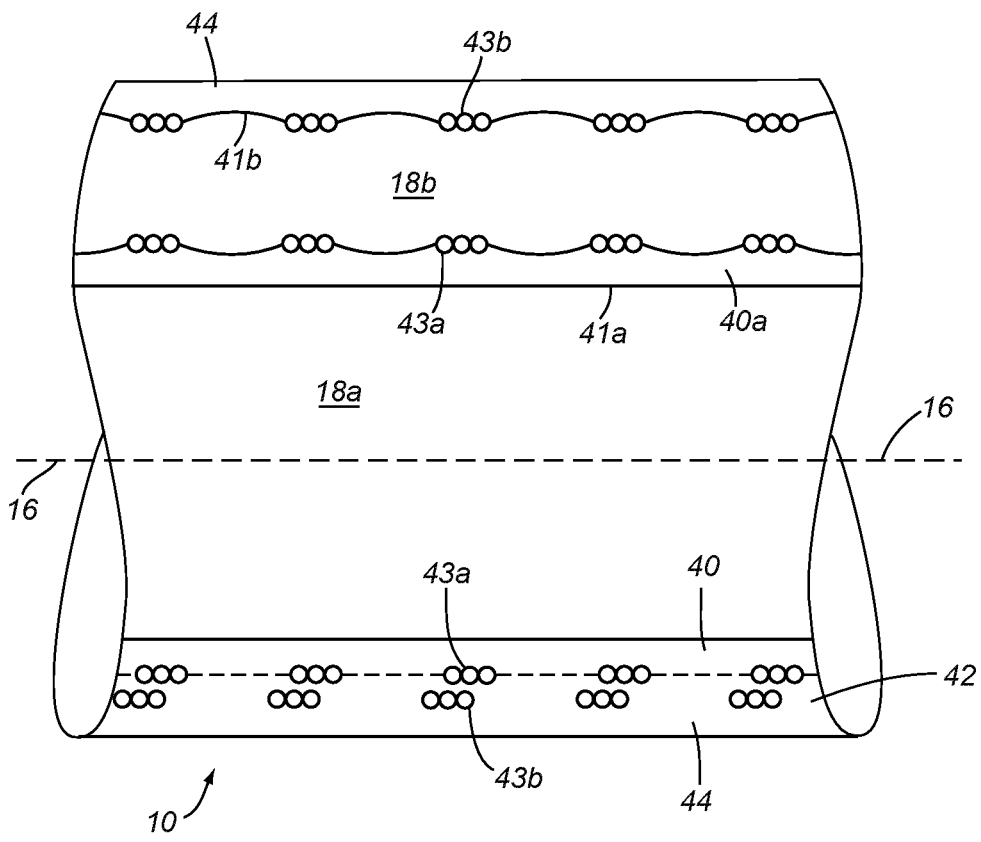
FIG. 1B is a cross-sectional side view of the catheter of FIG. 1A, taken along line 1B-1B, showing reinforcement members positioned around primary and auxiliary lumens of the catheter.

Turning to the drawings, FIGS. 1A and 1B show an exemplary embodiment of an apparatus 10 for introduction into a body lumen (not shown), e.g., for performing a diagnostic and/or therapeutic procedure within a patient's body. In exemplary embodiments, the apparatus 10 may be a guide catheter, a sheath, a procedure catheter, e.g., an imaging catheter, an ablation and/or mapping catheter, a balloon catheter, or other tubular device sized for introduction into a body lumen, such as a vessel within a patient's vasculature, a passage within a patient's gastrointestinal tract, urogenital tract, reproductive tract, respiratory tract, lymphatic system, and the like (not shown). In exemplary embodiments, the apparatus 10 may have a length between about ten and one hundred thirty centimeters (10-130 cm), and an outer diameter between about four and twenty-four French (4-24 Fr or 1.33-8.0 mm).

Generally, the apparatus 10 is an elongate tubular member including a proximal end 12, a distal end 14 sized for insertion into a body lumen, a central longitudinal axis 16 extending between the proximal and distal ends 12, 14, and one or more lumens 18 extending between the proximal and distal ends 12, 14. For example, as shown in FIG. 1B, the apparatus 10 may include a central or primary lumen 18a, e.g., sized for receiving or carrying one or more instruments or other elements (not shown). In exemplary embodiments, the central lumen 18a may be sized for receiving or carrying a guide wire, procedure catheter, balloon catheter, ablation catheter, cardiac lead, needle, or other instrument (not shown), one or more wires or other conductors, one or more optical fibers, one or more tubes or accessory lumens, one or more mechanical elements, one or more sensors, and/or sized for delivering and/or removing fluids or other flowable agents or materials therethrough.

In one embodiment, shown in FIG. 1A, the central lumen 18a may exit at or communicate with an outlet 17 in the distal end 14, e.g., to allow a guidewire or other instrument (not shown) to pass therethrough and/or for delivering or aspirating fluid therethrough. Alternatively, the central lumen 18a may be enclosed, e.g., terminating within or adjacent the distal end, e.g., by an electrode, cap, or other component (not shown) to isolate the central lumen 18a and/or elements carried therein from the environment outside the apparatus 10.

Figures 5, 6:
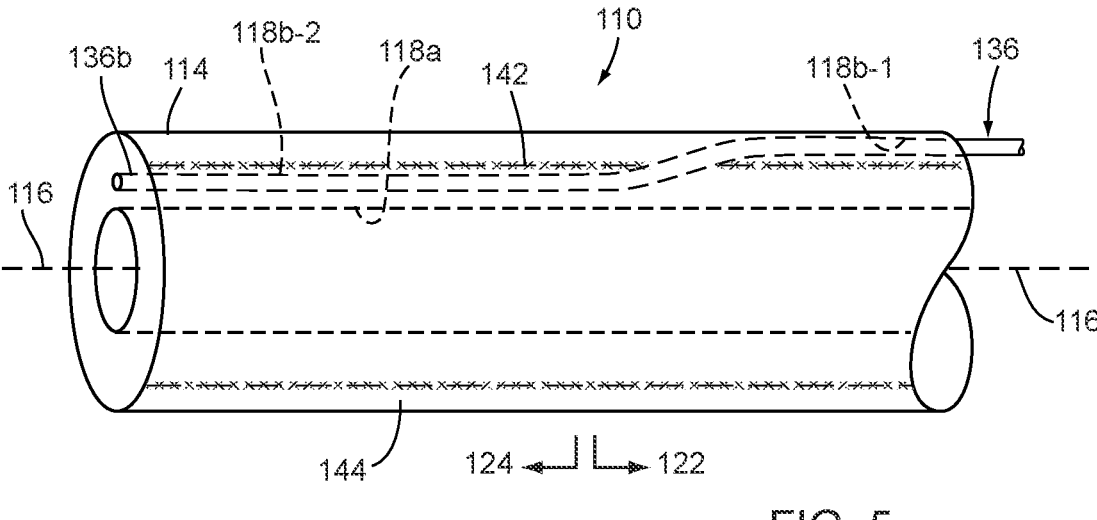
FIG. 5 is a partial cross-sectional side view of an exemplary embodiment of a catheter including a steering lumen for receiving a steering element.
FIG. 6 is a partial cross-sectional side view of another embodiment of a catheter including a plurality of electrodes mounted thereon and including a lumen for receiving one or more conductors for coupling to the electrodes.

Returning to FIG. 1B, in addition to the central lumen 18a, the apparatus 10 includes an auxiliary lumen 18b, e.g., extending adjacent the central lumen 18a, e.g., substantially parallel to and radially offset relative to the central axis 16. For example, in FIG. 5, an exemplary embodiment of a catheter 110 is shown in which the auxiliary lumen 118b may be a steering element lumen configured to receive a pull wire or other steering element 136 therein, e.g., to bend or otherwise deflect a distal portion of the catheter 110, as described further below. In FIG. 6, an exemplary embodiment of a catheter 210 is shown in which the auxiliary lumen 218$b$ may receive one or more wires or conductors 236 for coupling to one or more electrodes 238 mounted on the distal portion of the catheter 210, also as described further below.

With continued reference to FIGS. 1A and 1B, optionally, the apparatus 10 may include one or more additional lumens (not shown), e.g., one or more additional steering element lumens, conductor lumens, inflation lumens (e.g., if the apparatus 10 includes one or more balloons, not shown on the distal end 14), and/or accessory lumens. For example, a pair of auxiliary lumens may be provided (not shown) on opposite sides of the apparatus 10, e.g., offset about one hundred eight degrees (180°) around the circumference of the apparatus 10.

Optionally, the auxiliary lumen(s) may have a variety of cross-sectional shapes and/or sizes, e.g., a substantially circular shape, an elliptical or oval shape, a substantially rectangular shape, a triangular shape, a pair of overlapping circles shape, and the like, e.g., similar to the devices disclosed in U.S. Publication No. 2014/0323964, the entire disclosure of which is expressly incorporated by reference herein. The shape and/or size of the auxiliary lumen(s) may be substantially uniform along the length of the apparatus 10 or may vary at different locations, as described elsewhere herein.

The auxiliary lumen 18$b$ is generally radially offset from the central axis 16 substantially along the length of the apparatus 10, e.g., entirely from the distal end 14 to the proximal end 12. In addition, the radial and/or circumferential position of the auxiliary lumen 18$b$ may change relative to the primary lumen 18$a$ and/or other components of the apparatus 10 at various locations along the length of the apparatus 10, as described elsewhere herein.

Returning to FIG. 1A, the distal end 14 may include a tapered, rounded, or otherwise shaped distal tip 15, e.g., to provide a substantially atraumatic tip and/or to facilitate advancement or navigation through various anatomy. In addition or alternatively, the distal end 14 may include one or more therapeutic and/or diagnostic elements, e.g., one or more balloons, stents, sensors, electrodes, ablation elements, thermocouples, steering mechanisms, imaging devices, helical anchors, needles, and the like (not shown), depending upon the particular intended application for the apparatus 10. Further, in addition or alternatively, the distal end 14 may include one or more markers or other features to enhance radiopacity and/or visibility under ultrasound, MRI or other imaging modalities, e.g., by mounting one or more platinum elements on the distal end 14, doping one or more regions of the distal end 14 with tungsten or barium sulfate, and/or other methods known in the art.

Optionally, as shown in FIG. 1A, the proximal end 12 may include a handle or hub 30, e.g., configured and/or sized for holding and/or manipulating the apparatus 10 from the proximal end 12. In addition, the handle 30 may include one or more ports, e.g., port 32$a$ communicating with the central lumen 18$a$, or other respective lumens (not shown). Optionally, the port 32$a$ may include one or more valves, e.g., a hemostatic valve (also not shown), which may provide a substantially fluid-tight seal, while accommodating insertion of one or more instruments or fluids into the central lumen 18$a$. Optionally, a side port (not shown) may be provided on the handle 30, e.g., for delivering fluid into and/or aspirating fluid from the primary lumen 18$a$, e.g., around an instrument inserted into the primary lumen 18$a$. Optionally, the handle 30 and/or proximal end 12 may include one or more connectors, such as luer lock connectors, electrical connectors, and the like, for connecting other devices (not shown) to the apparatus 10, such as syringes, displays, controllers, and the like (also not shown).

In addition, the handle 30 may include one or more actuators, such as sliders, buttons, switches, rotational actuators, and the like, e.g., for activating and/or manipulating components (also not shown) on the distal end 14 or otherwise operating the apparatus 10. For example, as shown in FIG. 1A, an actuator 34 may be provided that is coupled to a proximal end of a steering element (not shown) within the auxiliary lumen 18$b$, e.g., similar to the embodiment shown in FIG. 5, as described further elsewhere herein.

Generally, with particular reference to FIG. 1B, the apparatus 10 may include an inner liner 40, e.g., at least partially or entirely surrounding or otherwise defining the central lumen 18$a$, a reinforcement layer 42 surrounding the inner liner 40, and an outer jacket 44 surrounding and/or encasing the reinforcement layer 42, each of which may extend at least partially between the proximal and distal ends 12, 14 of the apparatus 10. The reinforcement layer 42 and/or outer jacket 44 may be attached to the inner liner 40, e.g., by laminating, adhering, adhesive bonding, ultrasonic welding, reflowing or other heating, and the like, as described elsewhere herein.

In an exemplary embodiment, the central lumen 18$a$ is defined by an inner liner 40$a$ including an inner surface 41$a$. The inner liner 40$a$ may be formed from lubricious material, e.g., PTFE, to provide a lubricious inner surface 41$a$. Alternatively, the inner liner 40 may be formed from one or more layers of thermoplastic or other polymeric material including one or more coatings on the inner surface 41$a$ having desired properties, e.g., a hydrophilic and/or lubricious coating, e.g., similar to the liners disclosed in U.S. Pat. Nos. 7,550,053 and 7,553,387, and U.S. Publication No. 2009/0126862, the disclosures of which are expressly incorporated by reference herein.

Optionally, as shown in FIG. 1B, an inner liner 40$b$ may also at least partially surround the auxiliary lumen 18$b$, which may be formed from a lubricious material and/or may include one or more coatings on its inner surface 41$b$, similar to the inner liner 40$a$. The inner surface 41$b$ of the auxiliary lumen 18$b$ may have a substantially uniform cross-section, as shown in FIG. 1B. Alternatively, the inner surface 41$b$ of the auxiliary lumen 18$b$ may have a textured or other variable cross-section along, e.g., along its length and/or about its circumference (not shown).

Optionally, any or all of the inner liner 40$a$, reinforcement layer 42, and/or outer jacket 44 may be formed from multiple layers of like or different materials (not shown), e.g., to provide desired material properties in the different portions of the apparatus 10. In an exemplary embodiment, the outer jacket 44 may be formed from PEBAX, nylon, urethane, and/or other thermoplastic material, e.g., such that the material of the outer jacket 44 may be heated and reflowed and/or otherwise formed around the components defining the lumens 18, e.g., as described elsewhere herein.

In one embodiment, one or more of the layers of the apparatus 10 may have a substantially homogenous construction between the proximal and distal ends 12, 14. Alternatively, the construction may vary along the length of the apparatus 10 to provide desired properties, e.g., between proximal, intermediate, and distal portions 20, 22, 24. For example, a proximal portion 20 of the apparatus 10 adjacent the proximal end 12 may be substantially rigid or semi-rigid, e.g., providing sufficient column strength to allow the distal end 14 of the apparatus 10 to be pushed or otherwise manipulated from the proximal end 12, while the distal portion 24 may be substantially flexible. As described further below, the distal portion 24 of the apparatus 10 may be steerable, i.e., may be bent, curved, or otherwise deflected substantially within a steering plane, as described further below.

Returning to FIG. 1B, the reinforcement layer 42 may include one or more reinforcing members, e.g., wound in a braided or other helical configuration around the inner liner 40*a*, e.g., using a braiding apparatus such as that shown in FIGS. 4A and 4B, and the outer jacket 44 may include one or more tubular layers surrounding the reinforcement layer 42 and/or between the reinforcement layer 42 and the inner liner 40*a*. In an exemplary embodiment, the reinforcement layer 42 may include one or more, or a plurality of, round or flat (e.g., rectangular, elliptical, or flat oval) wires, filaments, strands, or other reinforcement members 43, e.g., formed from metal, such as stainless steel, plastic, such as PEEK, glass, woven or twisted fibers, such as aramid, and the like, or composite materials.

In one embodiment, a plurality of reinforcement members 43 may be braided around the inner liner 40*a*, e.g., with each reinforcement member 43 having the same material and/or shape. Alternatively, the reinforcement members 43 may have different sizes and/or shapes, e.g., a first size or shape extending helically in a first direction and a second size or shape (different than the first) extending helically in a second direction (e.g., opposite the first direction).

The reinforcement layer 42 may be configured to substantially transfer torsional forces between the proximal and distal ends 12, 14, e.g., to allow the apparatus 10 to be twisted from the proximal end 12 to rotate the distal end 14 about the longitudinal axis 16 within a patient's body. In addition, the reinforcement layer 42 may allow the distal end 14 of the apparatus 10 to be advanced or otherwise manipulated within a patient's body from the proximal end 12 without substantial risk of buckling and/or kinking. The pitch of the reinforcement layer 42 may be varied along the length of the apparatus 10, e.g., in order to optimize mechanical properties of various segments or portions of the apparatus 10.

Figure 2:
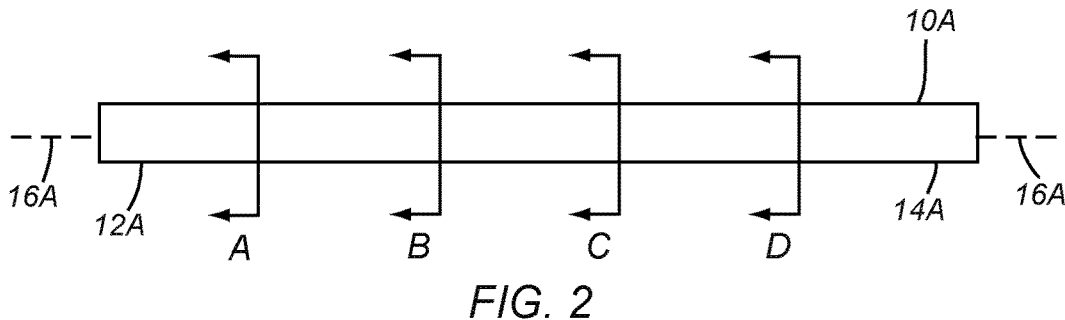
FIG. 2 is a side view of a first example of a catheter including a primary lumen and an auxiliary lumen that changes position along the length of the catheter.
Figures 2A, 2B, 2C, 2D:
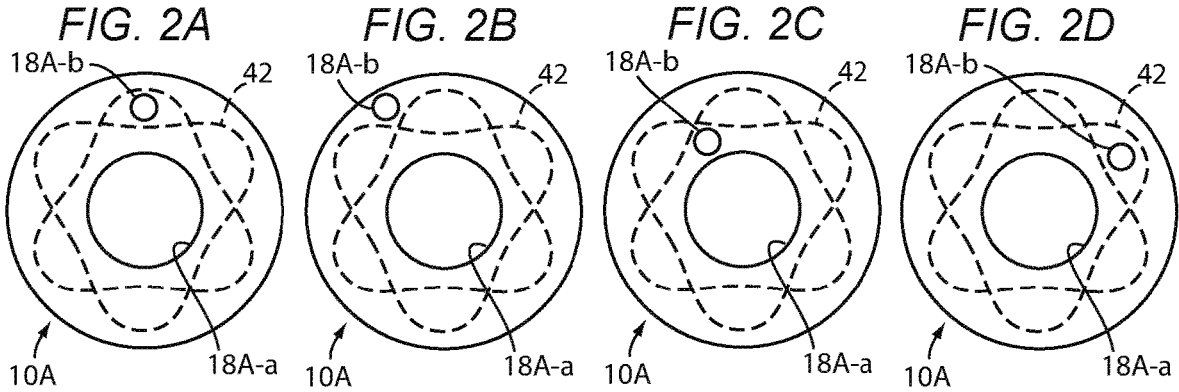
FIGS. 2A-2D are cross-sectional views of the catheter of FIG. 2 taken at different locations along the length of the catheter.

In addition, the location of the reinforcement layer 42 may vary relative to the central lumen 18*a* and/or auxiliary lumen 18*b*, e.g., as the auxiliary lumen 18*b* transitions to different radial locations within the wall of the apparatus 10. For example, FIG. 2 shows an example of a catheter 10A that includes a central lumen 18A-a that extends substantially along a central axis 16A and is surrounded by a reinforcement layer 42, which may be similar to any of the embodiments described elsewhere herein. In addition, the catheter 10A includes an auxiliary lumen 18A-b that extends between proximal and distal ends 12A, 14A of the catheter 10A adjacent the central lumen 18A-a at different radial and/or circumferential locations. As shown in FIG. 2A, along a proximal portion, the auxiliary lumen 18A-b may be braided into the reinforcement layer 42, while, as shown in FIG. 2B, at an intermediate portion, the auxiliary lumen 18A-b may transition outside the reinforcement layer 42. Further, as shown in FIG. 2C, the auxiliary lumen 18A-b may transition to a location closer to the central lumen 18A-a such that the reinforcement layer 42 surrounds both lumens 18A-a, 18A-b. Finally, as shown in FIG. 2D, the auxiliary lumen 18A-b may transition again and be braided into the reinforcement layer 42 along a distal portion to the distal end 14A.

With continued reference to FIGS. 2 and 2A-D, in an exemplary embodiment, a deflectable catheter shaft may be constructed wherein one or more auxiliary lumens 18A-b (e.g., a single auxiliary lumen or two auxiliary lumens spaced approximately one hundred eighty degrees (180°) apart) may be braided into or within the reinforcement layer 42 as shown in FIG. 2D at an intermediate portion (e.g., corresponding to FIG. 2 sections B and/or C) while the auxiliary lumen 18A-b may transition outside the reinforcement layer 42 as shown in FIG. 2B at a distal and proximal location (e.g., corresponding to FIG. 2 sections A and D). Additionally, the auxiliary lumen(s) 18A-b may pass through a jacket layer (as described elsewhere herein) overlying the reinforcement layer at or near the point(s) of transition from within to outside of the reinforcement layer 42.

In a further exemplary embodiment, the auxiliary lumen(s) 18A-b may pass through a jacket layer at or near the proximal transition(s) from within to outside the reinforcement layer and may terminate under or within the jacket layer at or near the distal transition(s) from within to outside the reinforcement layer, e.g., such that an actuator wire ring (not shown) with actuator wire(s) (not shown) attached may be positioned adjacent the distal point(s) of transition with actuator wire(s) travelling through the auxiliary lumen(s) 18A-b over the intermediate portion, the actuator wire ring being positioned under the jacket adjacent the distal transition and the actuator wire(s) exiting the a wall of the shaft through the jacket adjacent the proximal transition(s). A handle, such as that shown in FIG. 1, may be positioned around the proximal exit(s) that includes one or more actuators attached or otherwise coupled to the actuator wires at this position.

With continued reference to FIGS. 2 and 2A-D, in another exemplary embodiment, a deflectable catheter shaft may be constructed wherein one or more auxiliary lumens 18A-b (e.g., a single auxiliary lumen or two auxiliary lumens spaced approximately one hundred eighty degrees (180°) apart) may be braided under the reinforcement layer 42 as shown in FIG. 2C at an intermediate portion (e.g., corresponding to FIG. 2 sections B and/or C) while the auxiliary lumen 18A-b may transition outside the reinforcement layer 42 as shown in FIG. 2B at a distal and proximal location (e.g., corresponding to FIG. 2 sections A and D). Additionally, the auxiliary lumen(s) 18A-b may pass through a jacket layer (as described elsewhere herein) overlying the reinforcement layer at or near the point(s) of transition from under to outside of the reinforcement layer 42.

In a further embodiment, the auxiliary lumen(s) 18A-b may pass through a jacket layer at or near the proximal transition(s) from under to outside the reinforcement layer and may terminate under or under the jacket layer at or near the distal transition(s) from under to outside the reinforcement layer, e.g., such that an actuator wire ring (not shown) with actuator wire(s) (not shown) attached may be positioned adjacent the distal point(s) of transition with actuator wire(s) travelling through the auxiliary lumen(s) 18A-b over the intermediate portion, the actuator wire ring being positioned under the jacket adjacent the distal transition and the actuator wire(s) exiting the a wall of the shaft through the jacket adjacent the proximal transition(s). A handle, such as that shown in FIG. 1, may be positioned around the proximal exit(s) and one or more actuators may be attached or otherwise coupled to the actuator wires at this position.

Figure 3:
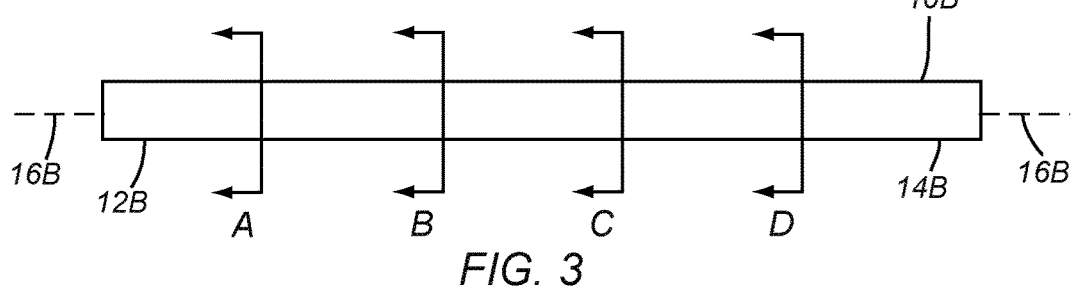
FIG. 3 is a side view of a second example of a catheter including a primary lumen and an auxiliary lumen that changes position along the length of the catheter.
Figures 3A, 3B, 3C, 3D:
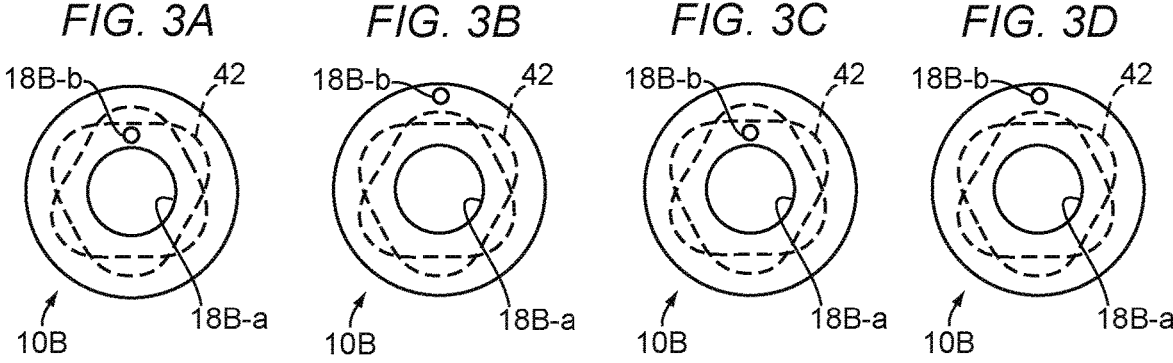
FIGS. 3A-3D are cross-sectional views of the catheter of FIG. 2 taken at different locations along the length of the catheter.

FIG. 3 shows another example of catheter 10B, similar to that shown in FIG. 2, e.g., including proximal and distal ends 12B, 14B extending between axis 16B, except that the auxiliary lumen 18B-b may extend along a proximal portion close to the central lumen 18B-a surrounded by the reinforcement layer 42 (as shown in FIG. 3A), may then transition and extend along an intermediate portion outside the reinforcement layer 42 (as shown in FIG. 3B), may again transition to a location surrounded by the reinforcement layer 42 (as shown in FIG. 3C), and finally may transition to a location outside the reinforcement layer 42 along a distal portion (as shown in FIG. 3D).

Thus, again with general reference to FIGS. 1A and 1B, in any of the apparatus and methods herein, it will be appreciated that the location of the auxiliary lumen 18*b* and/or reinforcement members 43 of the reinforcement layer 42 may be changed along the length of the apparatus 10 to provide desired mechanical and/or other performance characteristics for the final apparatus.

For example, with reference to FIG. 5, an apparatus 110 is shown in which a distal portion 124 of the apparatus 10 is steerable, e.g., using one or more pull wires, cables, fibers, threads, filaments, or other steering elements, such as a pull wire 136 slidably received within auxiliary lumen 118*b*. The steering element 136 generally includes a proximal end (not shown) coupled to an actuator, e.g., such as the actuator 34 on the handle 30 shown in FIG. 1, and extends from a proximal portion (not shown) through an intermediate portion 122 and into the distal portion 124. A distal end 136*b* of the steering element 136 may be fixed or otherwise coupled to the distal end 114, e.g., to a component defining or adjacent the distal tip (not shown).

The steering element 136 may be formed from materials capable of substantially transferring any axial forces applied at the proximal end to the distal end 114, as is known in the art. Optionally, the steering element 136 may include a coating, e.g., PTFE, parylene, silicone, or other lubricious material, an outer sleeve, e.g., formed from HDPE, PTFE, and the like, to reduce friction between the steering element and the wall of the auxiliary lumen 18*b*. Alternatively or in addition, the inner surface of the auxiliary lumen 118*b* may be formed from lubricious material and/or may include one or more coatings, as described elsewhere herein. Alternatively or in addition, the auxiliary lumen 18*b* may include one or more incompressible elements, e.g., a tightly wound coil therearound, e.g., to prevent compression, which may otherwise lead to creating a bending moment along at least part of its length.

During use, the actuator may be activated, e.g., directed proximally or distally relative to the handle and/or the proximal end (not shown), to apply an axial force to the steering element 136, e.g., tension (when the steering element is pulled) or compression (when the steering element is advanced). Because the steering element 136 is slidable within the auxiliary lumen 118*b*, the axial force is translated and applied to the distal end 136*b* coupled to the distal end 114. Further, because the auxiliary lumen 118*b* is offset from the central axis 116 along at least the distal portion 124, the axial force applies a bending moment, thereby causing the distal portion 124 to curve or otherwise bend in a desired plane or other manner. Optionally, the proximal and intermediate portions 122 of the apparatus 110 may be constructed to prevent or minimize bending forces caused by actuation of the steering element 136.

In the configuration shown in FIG. 5, along the distal portion 124, a second segment 118*b*-2 of the auxiliary lumen 118*b* may be surrounded by the reinforcement layer 142, e.g., immediately adjacent the central lumen 118*a* (e.g., similar to the location shown in FIG. 3A), and then may transition such that a first segment 118*b*-1 of the auxiliary lumen 118*b* is outside the reinforcement layer 142, e.g., closer to an outer surface of the apparatus 110 along at least the intermediate portion 122 (and/or optionally along the proximal portion to the proximal end and/or handle, not shown). Alternatively, the second segment 118*b*-2 may be braided into the reinforcement layer 142 (e.g., similar to the location shown in FIG. 2A), which is surrounded by outer layer 144.

Locating the second segment 118*b*-2 surrounded by the reinforcement layer 142 may enhance performance properties of the steering element 136 and/or may reduce the risk of the steering element 136 tearing through the wall of the distal portion 124, e.g., when a proximal force or tension is applied to the steering element 136. Locating the first segment 118*b*-1 outside the reinforcement layer 142 may facilitate accessing the auxiliary lumen 118*b*, e.g., during manufacturing and/or assembly, to couple the proximal end of the steering element 136 to an actuator and/or other components (not shown) at the proximal end of the apparatus 110.

Conversely, if the apparatus 110 were intended to include one or more sensors, actuators, electrodes, imaging element, or other components on the distal portion, the configuration could be reversed. For example, the location of the second segment 118*b*-2 of the auxiliary lumen 118*b* may extend from a proximal end of the apparatus 110 to a distal portion and then may transition to the location of the first segment 118*b*-1, e.g., outside the reinforcement layer 142 along the distal portion. This configuration may facilitate accessing the auxiliary lumen 118*b* at the distal portion, e.g., to couple one or more wires or conductors disposed within the second segment 118*b*-2 of the auxiliary lumen 118*b* to the sensors, actuators, electrodes, imaging elements, and/or or other components, e.g., since the auxiliary lumen 118*b* is closer to the outer surface of the apparatus 10. Along the proximal and/or intermediate portions, the auxiliary lumen 118*b* and consequently the conductor(s) may be disposed deeper within the apparatus 110, e.g., beneath and/or within the reinforcement layer 142, which may at least partially shield or otherwise protect the conductor(s).

Turning to FIG. 6, in another embodiment, an apparatus 210 may be provided that includes a plurality of sensors, actuators, electrodes, imaging elements, and/or or other components 238 on a distal portion 224 of the catheter 210, which may be coupled to one or more wires or conductors 236 extending through an auxiliary lumen 218*b* proximally from the distal portion 224, e.g., from the distal end 214 to one or more connectors and/or electronics at the proximal end (not shown) of the apparatus 210.

In the exemplary embodiment shown, the auxiliary lumen 218*b* may extend generally along the distal portion 224 braided into the reinforcement layer (e.g., similar to the location shown in FIG. 2A) or completely surrounded by the reinforcement layer (e.g., similar to the location shown in FIG. 3A) as represented by segments 218*b*-1, but may transition to segments 218*b*-2 that are positioned outside the reinforcement layer (e.g., similar to the location shown in FIG. 3B) for a relatively short distance, e.g., under the locations intended for the electrodes 238. With the auxiliary lumen 218*b* closer to the outer surface at the short segments 218*b*-2, any wires or conductors within the auxiliary lumen 218*b* may be easily accessed during manufacturing or assembly, e.g., to expose and couple the electrodes 238 to the conductor(s) when the electrodes 238 are mounted to the distal portion 224. Otherwise, the conductor(s) may be located relatively deep within the apparatus 210.

Alternatively, the lumen configuration shown in FIG. 6 may be adapted to provide a series of side ports in the distal portion 224 in fluid communication with a proximal portion of the catheter (not shown) by way of an unoccupied auxiliary lumen 218*b*, e.g., such that fluid may delivered through the auxiliary lumen 218*b* and out the side ports and/or aspirated into the auxiliary lumen 218*b* through the side ports from a location outside the distal portion 224.

Figure 7A:
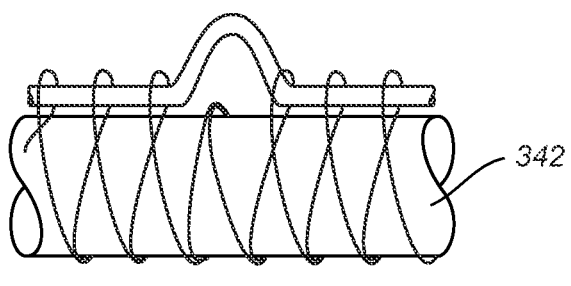
FIG. 7A is a side view of a portion of a catheter subassembly including a primary mandrel and a secondary mandrel wrapped by reinforcement members and including a section of the secondary mandrel that has been pulled outside the reinforcement members.
Figure 7B:
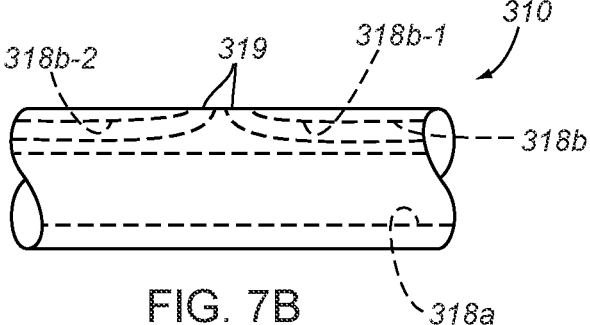
FIG. 7B is a side view of a portion of a catheter resulting from the catheter subassembly of FIG. 7A that includes a discontinuous auxiliary lumen that communicates with side openings in the wall of the catheter.

In yet another embodiment, shown in FIGS. 7A and 7B, an apparatus 310 may be provided that includes a discontinuous auxiliary lumen 318*b* adjacent a central lumen 318*a*. For example, as shown in FIG. 7B, a first segment 318*b*-1 of the auxiliary lumen 318*b* may extend proximally from a predetermined location, e.g., to a proximal portion of the apparatus 310 and a second segment 318*b*-2 may extend distally from the predetermined location such that both segments communicate with side openings 319 disposed adjacent one another. The auxiliary lumen 318*b* may be braided into a reinforcement layer 342, e.g., as shown in FIG. 7A, or disposed at other positions relative to the central lumen 318*a*, as described elsewhere herein.

Turning to FIGS. 4A-4C, various methods may be used for manufacturing and/or assembling any of the embodiments described herein. For example, FIG. 4A shows an exemplary embodiment of an apparatus 50 for making one or more tubular bodies, such as catheters and/or components for catheters, sheaths, or other tubular devices 8. Generally, the apparatus 50 includes a plurality of sources 52, 54 of mandrels 2 and/or liners 4, a guide 60, a source 70 of reinforcement members 6, a drive mechanism 80, and, optionally, a source 90 of jacket material 7.

While mandrels, liners, and/or jackets may be provided in discrete segments (not shown), the apparatus 50 may allow for substantially continuous fabrication of tubular bodies, e.g., wrapping a liner material 4*a* around a primary mandrel 2*a* (or the primary mandrel 2*a* may include a tubular or other liner material provided around it on the source 52, e.g., similar to the liners disclosed in the references incorporated by reference elsewhere herein), positioning an auxiliary mandrel 2*b* (with optional liner material, not shown) adjacent the primary mandrel 2*a*, braiding a plurality of reinforcement members 4 around the mandrels 2, and optionally, applying outer jacket material 7 around the reinforced mandrels, as described further below.

As used herein, "substantially continuous" means that the apparatus 50 and/or method may operate indefinitely, i.e., to make as few as one or as many as hundreds or thousands of tubular bodies 8, e.g., by substantially simultaneously feeding components of the tubular bodies 8 from sources 52, such as reels, through components of the apparatus 50 until the sources 52 are depleted, whereupon new source(s) may be loaded onto the apparatus 50 and the process continued. Alternatively, the apparatus 50 may be used to create discrete lengths of tubular devices, e.g., if the mandrels and/or liners are provided in specific lengths corresponding to one or more individual tubular devices (not shown). In a further alternative, some of the operations may be performed substantially continuously, while other operations are performed on components intended for one or more individual tubular devices.

Thus, the apparatus 50 and methods herein may be used to make one or more relatively long tubular bodies 8, e.g., that are substantially longer than finished catheters or other tubular devices. For example, one resulting tubular body 8 may be collected, e.g., on a take-up reel or container (not shown), or may be separated into individual shorter tubular bodies, e.g., using a cutter or other tool (not shown), that may be incorporated into individual catheters or other tubular devices, e.g., as described elsewhere herein and/or as disclosed in U.S. Publication No. 2009/0126862, the entire disclosure of which is expressly incorporated by reference herein.

With particular reference to FIG. 4A, the apparatus 50 may include one or more sources 52 of mandrels 2 and, optionally, one or more sources 54 of liner material 4, which may be fed into a guide 60 to define lumens of the tubular bodies 8. For example, a first reel 52*a* may include an elongate primary mandrel 2*a*, e.g., shaped and/or configured to define a primary or central lumen (not shown) of the tubular bodies 8. Similarly, a second reel 52*b* may include an elongate auxiliary mandrel 2*b*, e.g., shaped and/or configured to define a secondary or auxiliary lumen (also not shown) of the tubular bodies 8. As described further below, the second reel 52*b* or other source of auxiliary mandrel may be located at one of a plurality of available locations during operation to configure the tubular bodies 8 in a desired manner. Optionally, if additional lumens are desired for the tubular bodies 8, one or more additional auxiliary mandrels may be provided (not shown), which may also be moved to one or more locations.

The mandrels 2 may have desired cross-sectional shapes and/or sizes corresponding to the desired cross-sections of the lumens, e.g., substantially circular or other shapes, as described elsewhere herein. The mandrels 2 may be a solid or hollow wire or other cylindrical member having a diameter (or other cross-section) corresponding to the diameter of the lumen to be lined by the strip 24, e.g., between about 0.005-0.300 inch (0.125-7.5 mm), 0.014-0.092 inch (0.35-2.3 mm), or 0.014-0.045 inch (0.35-1.15 mm). In an exemplary embodiment, the auxiliary mandrel 2*b* may have a substantially smaller diameter or other cross-section than the primary mandrel 2*a*. In exemplary embodiments, the mandrels 2 may be formed from beading or monofilament material, for example, lubricious material, e.g., PTFE or other fluoropolymer, silicone-treated Acetal, PTFE-coated stainless steel, Parylene-coated stainless steel, silver coated copper, and the like, having sufficient flexibility to allow the mandrels 2 to be wound onto a source reel 52 and/or onto a take-up reel (not shown) after being incorporated into a tubular body 8.

Alternatively or in addition, the mandrels 2 may have a tubular liner predisposed about them, e.g. a fluoropolymer sleeve or coating or other tubular material which may facilitate removal of the mandrel 2 and/or be left behind upon removal of the mandrel 2 to form a liner. Further alternatively, a shim (not shown) may be positioned over a mandrel 2 and/or within a tubular or strip liner such that the shim (not shown) may facilitate creation of a lumen that is larger than the mandrel 2 with or without ultimate removal of the mandrel 2. For example, a PTFE tube or strip shim (not shown) may be positioned around a mandrel 2 and inside of a strip or tubular liner. The mandrel/shim/liner assembly may then be incorporated into a braided shaft or finished apparatus. The shim (not shown) may be subsequently removed, e.g. after braiding, lamination, etc. to leave a lumen larger than the mandrel. After this, the mandrel may remain in place, for example in the case of the auxiliary mandrel 2*b* to serve as a pull wire, or simply removed with less force.

In an alternative embodiment, the mandrels 2 may be formed from material that substantially maintains its size and shape during fabrication of the tubular bodies, yet may be reduced in cross-section after fabrication to facilitate removal. For example, silver-coated copper wire, PTFE beading, or other malleable metals or polymers may be used for the mandrels 2 that, after fabrication of the tubular body

8, may be necked down before and/or during removal. For example, after fabricating a tubular body 8, the mandrels 2 (or the entire tubular body) may be pulled at one or both ends, thereby causing the mandrels 2 to plastically elongate and thereby reduce their outer cross-section slightly, which may reduce friction between the mandrels 2 and the surrounding liners, reinforcement members, and/or other materials, and thereby facilitate removal. Further alternatively, the mandrels 2 may include a rolled strip with inherent radial strength capable of supporting a lumen during braiding and/or lamination and/or other processing, but may subsequently be constrained, stretched, or otherwise removed. Further alternatively, the mandrels 2 may be constructed from material having relatively high thermal expansion such that during heating, lamination, and/or reflow, the mandrels 2 expand and upon cooling contract, thereby creating a lumen larger than the original mandrel 2.

In yet another alternative, the mandrels 2 may be formed from materials that may be dissolved, e.g., after fabrication, leaving the surrounding materials intact to define the lumens.

In still another alternative, tubular mandrels may be used that have sufficient hoop strength to resist deformation under the forces encountered during braiding and/or other fabrication and/or heating or other processing parameters experienced during fabrication. In this alternative, the tubular mandrels may remain substantially within the tubular bodies 8 after fabrication, e.g., to define the auxiliary lumen. For example, a relatively thick walled PTFE, a lined or bare polyimide tube, or other tubular mandrel may be used. Alternatively, the inner diameter of such a tubular mandrel may be temporarily supported by a temporary supporting mandrel (not shown), e.g. during braiding, and the temporary supporting mandrel may be removed prior to subsequent fabrication and/or heating or other processing steps, e.g., if the tubular mandrel is to remain as a permanent component of the tubular bodies.

Optionally, a source 54 of liner material 4 may be provided for the one or both mandrels 2. For example, as shown, a source 54a of liner material 4a is provided such that the liner material 4a may be wrapped at least partially around the primary mandrel 2a, e.g., as the primary mandrel 2a and liner material 4a are fed through the guide 60. The liner material 2a may be formed from lubricious material and/or may include one or more coatings (not shown) on an inner surface thereof oriented towards the primary mandrel 2a, which may provide an inner liner for a primary lumen of the resulting tubular bodies 8a.

For example, the liner material may include a base material, e.g., a relatively thin-walled polymer sheet having a width corresponding to the circumference of the corresponding mandrel, e.g., thermoplastics, such as polyether block amide, urethane, nylon, and the like, fluoropolymers, such as PTFE, FEP, TFE, and the like, thermoset, and thermoform plastics, such as polyimide or polyester, and the like. In exemplary embodiments, the liner material may have a thickness between about 0.0001-0.050 inch (0.0025-1.25 mm), 0.0001-0.003 inch (0.0025-0.076 mm), 0.0001-0.0015 inch (0.0025-0.038 mm), or 0.0005-0.002 inch (0.0125-0.05 mm).

Optionally, if desired a source of liner material may also be provided for the auxiliary mandrel 2b and/or for other auxiliary mandrels (not shown for simplicity). In this option, a guide (not shown) may be provided for wrapping the liner material around the auxiliary mandrel 2b, e.g., before the auxiliary mandrel 2b is positioned adjacent the primary mandrel 2a. In an alternative embodiment, tubular liner material may be provided on one or both mandrels s when loaded on the source 52, and/or may be fed onto the desired mandrel in discrete segments (not shown) before passing the mandrels 2 through the guide 60 or horn gear 72.

With additional reference to FIGS. 4A and 4B, the source 70 of reinforcement members 6 may provide one or more, e.g., a plurality of, reinforcement members 6 that may be wrapped around the mandrels 2, e.g., upon exiting the guide 60. In the exemplary embodiment shown in FIG. 4B, the reinforcement source 70 may include an arrangement of horn gears 72, e.g., mounted in a generally circular configuration around the guide 60, for example, to a base or other support structure 76. The horn gears 72 may be free to rotate about their individual central axes but may be substantially fixed translationally relative to one another and the guide 60. The horn gears 72 may pass one or more carriers 74 of reinforcement members 6 around the path 78, e.g., in a clockwise and/or counterclockwise direction, e.g., with at least some of the carriers travelling clockwise and some travelling counterclockwise, e.g., to create a braided pattern. The carriers 74 may be loaded onto the horn gears to create a variety of patterns, e.g., one-over-one-under (diamond pattern), two-over-two-under (herring bone pattern), one-over-one-under with two reinforcement members running side by side (tow), and/or other patterns, as are known in the art.

Alternatively, the horn gears 72 may be rotatable relative to the guide 60 and/or primary mandrel 2a, e.g., around a central axis of the guide 60, e.g., along a path 78 shown in FIG. 4B, while maintaining their same circular configuration, e.g., by rotating the base 76 relative to the guide 60, as described further elsewhere herein.

In addition, the auxiliary mandrel 2b may be moved to different locations relative to the horn gears 72, e.g., to position the auxiliary mandrel 2b relative to the primary mandrel 2a and/or reinforcement members 6. For example, as shown in FIG. 4B, during operation of the apparatus 50, the source of auxiliary mandrel 2b may be positioned at locations A1, A2, or A3, e.g., for a predetermined time and/or distance along the primary mandrel 2a, and, as desired, moved to one of the other locations one or more times. Thus, in this manner, the location of the auxiliary mandrel 2b may be adjusted, which may result in the location of an auxiliary lumen defined by the auxiliary mandrel 2b being moved to desired locations, as shown in FIG. 4C and as described elsewhere herein.

For example, in position A1 shown in FIG. 4A, one of the horn gears 72a may include a passage 73a therethrough, e.g., aligned with the central axis of the horn gear 72a, and the auxiliary mandrel 2b may pass through the passage 73a, e.g., from the source 52b towards the primary mandrel 2a where it exits the guide 60. If liner material is wrapped or otherwise disposed around the auxiliary mandrel 2b, a guide (not shown) may be provided before, after, or within the passage 73a to wrap or otherwise dispose the liner material around the auxiliary mandrel 2b. Optionally, if additional auxiliary lumens are to be provided in the tubular bodies 8, one or more additional horn gears may also include such passage(s) and/or guide(s) for guiding corresponding auxiliary mandrel(s) therethrough.

As described further below, in this location, the auxiliary mandrel 2b may be at least partially braided into the reinforcement members 6 adjacent the primary mandrel 2a, i.e., with some reinforcement members 6 surrounding both the primary mandrel 2a and the auxiliary mandrel 2b, and some reinforcement members 6 surrounding only the primary mandrel 2a, as identified by auxiliary mandrels A1 shown in FIG. 4C. By comparison, in location A2, i.e., with the auxiliary mandrel 2b directed immediately adjacent the primary mandrel 2a, e.g., through the guide 60, all of the reinforcement members 6 may surround both the primary mandrel 2a and the auxiliary mandrel 2b, thereby positioning the auxiliary mandrel 2b closest to the primary mandrel 2a along the tubular device 8. Finally, in location A3, i.e., with the auxiliary mandrel 2b outside the path of the horn gears 72, e.g., outside the path 78 shown in FIG. 4B, or otherwise directed towards the primary mandrel 2a after the braiding operation, all of the reinforcement members 6 may only surround the primary mandrel 2a and the auxiliary mandrel 2b may remain outside all of the reinforcement members 6, e.g., closest to the outer surface of the tubular device 8 shown in FIG. 4C.

Optionally, if desired, individual carriers may be loaded with multiple reinforcement members (not shown), e.g., such that multiple reinforcement members are braided adjacent one another in each direction from each carrier. For example, with the auxiliary mandrel 2b directed from location A1, a first set of reinforcement members 43a may travel and be braided in a first direction by the horn gears 72 such that all of the windings of the first set 43a pass between the auxiliary mandrel 2b and the primary mandrel 2a at that specific horn gear. A second set of reinforcement members 43b may travel and be braided in a second opposite direction by the horn gears 72 such that all of the windings of the second set 43b pass over the auxiliary mandrel 2b at that specific horn gear. Otherwise, the reinforcement members may pass over and under one another according to the arrangement of horn gears 72 and carriers 74 loaded onto the reinforcement source 70, which pattern generally alternates at each subsequent horn gear, e.g., as described in U.S. Publication No. 2014/0323964, incorporated by reference herein.

In addition, with the auxiliary mandrel 2b in position A1, one of the horn gears 72a may include a passage 73a therethrough, e.g., aligned with the central axis of the horn gear 72a, and the auxiliary mandrel 2b may pass through the passage 73a, e.g., from the source 52b towards the primary mandrel 2a where it exits the guide 60. If liner material is wrapped or otherwise disposed around the auxiliary mandrel 2b, a guide (not shown) may be provided before, after, or within the passage 73a to wrap or otherwise dispose the liner material around the auxiliary mandrel 2b.

Optionally, if additional auxiliary lumens are to be provided in the tubular bodies 8, one or more additional horn gears may also include such passage(s) and/or guide(s) for guiding corresponding auxiliary mandrel(s) therethrough, e.g., to provide auxiliary mandrel(s) in location A1, or additional auxiliary mandrel(s) may be provided at locations A2 and/or A3, as desired.

With further reference to FIG. 4A, as can be seen, the primary mandrel 2a may exit the guide 60 with the liner material 4a being wrapped substantially around the primary mandrel 2a. With the auxiliary mandrel 2b directed from the desired location, the auxiliary mandrel 2b may be directed towards the primary mandrel 2a such that the auxiliary mandrel 2a is disposed adjacent the primary mandrel 2a, e.g., before braiding (location A2), braided into the reinforcement members 6 (location A1), or after braiding (location A3).

At any time, the auxiliary mandrel 2b may be moved to a different location than its current one to transition the auxiliary mandrel 2b to the desired position relative to the primary mandrel 2a and/or reinforcement members 6. Thus, in this manner, all of the reinforcement members 6 may surround the primary mandrel 2a, while all, some, or none of windings 43a may surround the auxiliary mandrel 2b, as shown in FIG. 4C. This transition may be performed substantially continuously, e.g. by directing the auxiliary mandrel 2b to the desired location after a predetermined length or portion of the tubular device 7 has been braided in the desired manner. Alternatively, discrete lengths or portions may be braided in the desired manner, e.g., by stopping the apparatus 50, removing and repositioning the auxiliary mandrel 2b to position the auxiliary mandrel 2b to the desired relative to the primary mandrel 2a and/or reinforcement members 6, and then resuming operation for a desired time and/or length. This process may be repeated as many times as desired, e.g., to produce tubular devices, such as the apparatus 10A, 10B shown in FIGS. 2 and 3.

Returning to FIGS. 4A and 4B, the drive mechanism 80 may include one or more components for pulling or otherwise directing the mandrels 2 through the apparatus 50. For example, the drive mechanism 80 may include a pair of spaced-apart rollers 82 coupled to a motor (not shown) that engage the reinforcement-wrapped mandrels 2 and apply sufficient tension to pull the mandrels 2 from their sources 52 through the guide 60 and/or horn gear 72a while the reinforcement members 6 are braided around the mandrels 2. Alternatively, the drive mechanism may be provided before the reinforcement members 6 are braided around the mandrels 2, e.g., pushing the primary mandrel 2a through the braiding operation and potentially pulling the auxiliary mandrel 2b by the braiding action itself. Optionally, other drive mechanisms and/or tension adjusters (not shown) may be provided for maintaining a desired tension and/or otherwise guiding the mandrels 2, liners 4, reinforcement members 6, and assembled device in a desired manner along the fabrication path.

Optionally, as shown in FIG. 4A, the jacket source 90 may be provided for applying one or more layers of jacket material around the reinforcement-wrapped mandrels 2. For example, a co-extruder, laminator, or other applicator may be provided that applies melted, uncured, and/or otherwise raw jacket material 7, e.g., from a hopper or other container (not shown), or rolls sheets of jacket material 7 may be wrapped around the reinforcement members 43 and mandrels 2. For example, for thermoplastic or other flowable materials, a heater (not shown) within a co-extruder may melt or otherwise soften the jacket material 7 to allow the jacket material 7 to flow around the reinforcement members 43 and into contact with the liner material 4 surrounding the mandrels 2 (or the mandrels 2 directly if no liner material is provided). Alternatively, the jacket material 7 may be a thermoset plastic or other material such that components of the jacket material 7 may be delivered into the co-extruder, e.g., as a liquid, powder, and the like, and mixed to form a slurry that is delivered around the reinforcement-wrapped mandrels 2. The components may chemically or otherwise react with one another and/or be heat fused to form a solid jacket 7 once cured. Exemplary materials for the jacket material 7 include plastics, e.g., thermoplastics, such as polyether block amide, nylon, or urethanes, thermoset plastics, metals, or composite materials. Alternatively, other processing may be used to bond or otherwise attach the jacket material 7 to the liner material 4 and/or embed the reinforcement members 43 in the jacket material 7, thereby resulting in an integral tubular body 8.

The resulting tubular body 8 (with or without jacket material 7) may be collected, e.g., on a capture reel or in a container (not shown). Thereafter, the tubular body 8 may be further processed to make a catheter, sheath, or other device.

For example, a cutter or other tool (not shown) may separate the tubular body 8 into individual tubular shafts, e.g., before or after removing the mandrels 2. For example, the mandrels 2 may remain within the tubular body 8 when cut into individual devices, and then may be removed, resulting in a primary lumen and an auxiliary lumen, e.g., similar to the apparatus 10 shown in FIG. 1B. Alternatively, if the friction between the mandrels 2 and the surrounding material is relatively low, the mandrels 2 may be removed before the tubular body 8 is cut into individual devices.

The resulting inner surface 41*a* of the primary lumen 18*a* may have a substantially uniform cross-section, e.g., as shown in FIG. 1B. Similar the auxiliary lumen 18*b* may also have a substantially uniform cross-section, e.g., also as shown in FIG. 1B or may have a variable cross-section, if desired (not shown).

Other components may be added to the individual tubular devices, as desired for the particular application. For example, for a steerable catheter, such as the apparatus 110 shown in FIG. 5, a steering element 136 may be inserted through the auxiliary lumen 118*b* (created when the auxiliary mandrel 2*b* is removed). In an alternative embodiment, the auxiliary mandrel 2*b* may remain within the tubular device to provide the steering element, e.g., if the friction between the outer surface of the auxiliary mandrel 2*b* and the liner or other material defining the auxiliary lumen are relatively low. A tip or other component (not shown) may be attached to a distal end 114 of the apparatus 110, e.g., after attaching the distal end 136*b* of the steering element 136 to the tip. The other end of the steering element may be coupled to an actuator of a handle attached to a proximal end of the tubular device, e.g., similar to the embodiment shown in FIG. 1A and described elsewhere herein.

For the apparatus 210 shown in FIG. 6, the auxiliary lumen 218*b* may be formed by positioning the auxiliary mandrel 2*b* in location A2 (shown in FIGS. 4B and 4C or optionally in location A1 for at least some portions) and generally braiding the reinforcement material 6 around both the primary and auxiliary mandrels 2*a*, 2*b*, except that at the segments corresponding to the locations of the electrodes 238, the auxiliary mandrel 2*b* may be moved to location A3 and then returned back to location A2 (or A1). After the outer layer 244 has been applied around the reinforcement members 242, the mandrels may be removed to provide an auxiliary lumen with segments 218*b*-1 braided into or under the reinforcement layer 242 other than segments 218*b*-2 at the electrode locations.

One or more wires 236 may be directed into the auxiliary lumen 218*b* (or may be used as the auxiliary mandrel, if desired), and the segments 218*b*-2 may be accessed, e.g., by cutting into the outer layer 244 to expose the wire(s), which may then be coupled to the electrodes 238 mounted on the apparatus 210.

Alternatively, the auxiliary mandrel 2*b* may remain at location A2 (or A1) for the entire length of the tubular body 8, and a segment of the auxiliary mandrel 2*b* may be manually (or automatically) pulled out from within the braid of the reinforcement members 6, as shown in FIG. 7A before applying the outer layer 244. In this alternative, the auxiliary lumen 318*b* may be discontinuous, i.e., communicating with side openings 319. One or more wire(s) may be directed into the auxiliary lumen 318*b* such that regions of the wire(s) exit and reenter the side openings 319. These regions may then be exposed and/or otherwise coupled to an electrode (not shown) mounted on the apparatus 310.

Figure 8A:
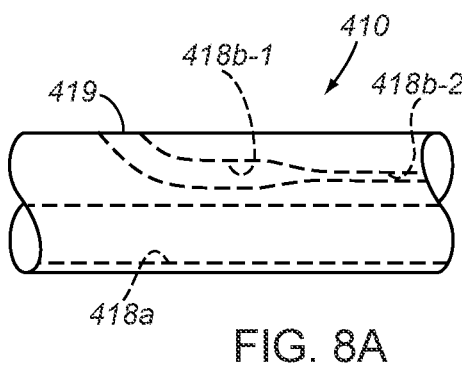
FIG. 8A is a side view of a portion of another embodiment of a catheter including an auxiliary lumen that has a variable diameter.
Figure 8B:
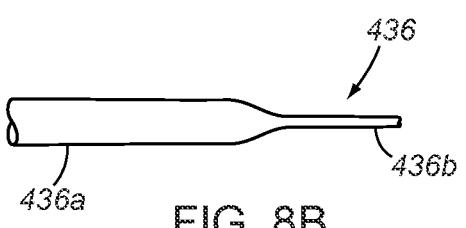
FIG. 8B is a side view of a portion of a steering element that may be received in the auxiliary lumen of the catheter of FIG. 8A.

Turning to FIGS. 8A and 8B, optionally, in any of the embodiments herein, the size of the auxiliary lumen 418*b* may be varied at desired locations along the apparatus 410, e.g., by using an auxiliary mandrel having a variable diameter or other cross-section (not shown). For example, in the apparatus 410 shown in FIG. 8A, an auxiliary lumen 318*b* is provided adjacent a central lumen 318*a*, which may be positioned relative to the central lumen 318*a* and/or reinforcement members (not shown), similar to other embodiments herein. As shown, the auxiliary lumen 418*b* includes a first or proximal segment 318*b*-1 having a first diameter and extending from a side opening 319 along a portion of the apparatus 410. The auxiliary lumen 418*b* then transitions to a second segment 418*b*-2 having a second diameter smaller than the first diameter.

Such an auxiliary lumen 418*b* may be formed using an auxiliary mandrel having regions 436*a*, 436*b* corresponding to the first and second diameters and lengths of the segments. As shown in FIG. 8B, a steering element 436 may be provided that has similar diameters and regions (e.g., slightly smaller than the first and second diameters). After removing the auxiliary mandrel, the steering element 436 may be loaded into the auxiliary lumen 418*b* through the side opening 419 and the distal segment (not shown) may be coupled to the distal end of the apparatus 410, similar to other embodiments herein. Alternatively, the auxiliary mandrel itself may be used as the steering element, also similar to other embodiments herein. This configuration may enhance pushability of the apparatus 410, e.g., since the proximal, larger segment may be relatively stiffer than the distal, smaller segment.

Figure 9:
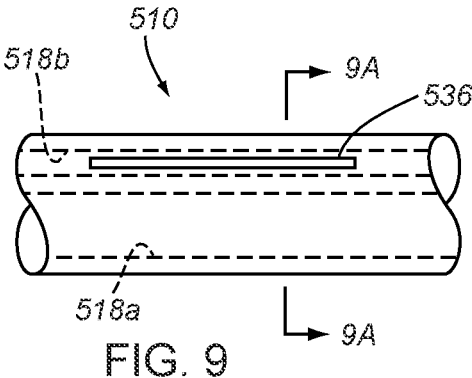
FIG. 9 is a side view of a portion of still another embodiment of a catheter including one or more stiffening elements embedded into a wall of the catheter.
Figure 9A:
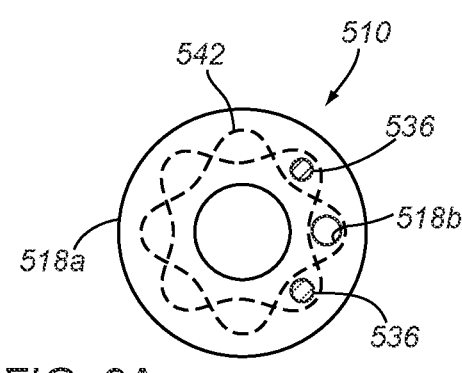
FIG. 9A is a cross-section of the catheter of FIG. 9 taken across 9A-9A.

Optionally, in any of the embodiments herein, one or more stiffening members may be added to desired portions of the apparatus. For example, FIGS. 9A and 9B show an exemplary embodiment of an apparatus 510 including a central lumen 518*a* and auxiliary lumen 518*b*, which may be surrounded and/or braided into a reinforcement layer 542, similar to other embodiments herein.

Unlike previous embodiments, a pair of stiffening members 536 have also been braided into the reinforcement layer 542. For example, with reference to the apparatus 50 in FIGS. 4A-4C, at desired portions of the tubular body 8, one or more stiffening members (not shown) may be directed adjacent the primary mandrel 2*a*, e.g., at positions similar to A1 (to braid the stiffening members into the reinforcement members 6. In this manner, the supported portion(s) may have greater column strength than other unsupported portions of the resulting apparatus 510.

Figures 10, 10A, 10B, 10C:
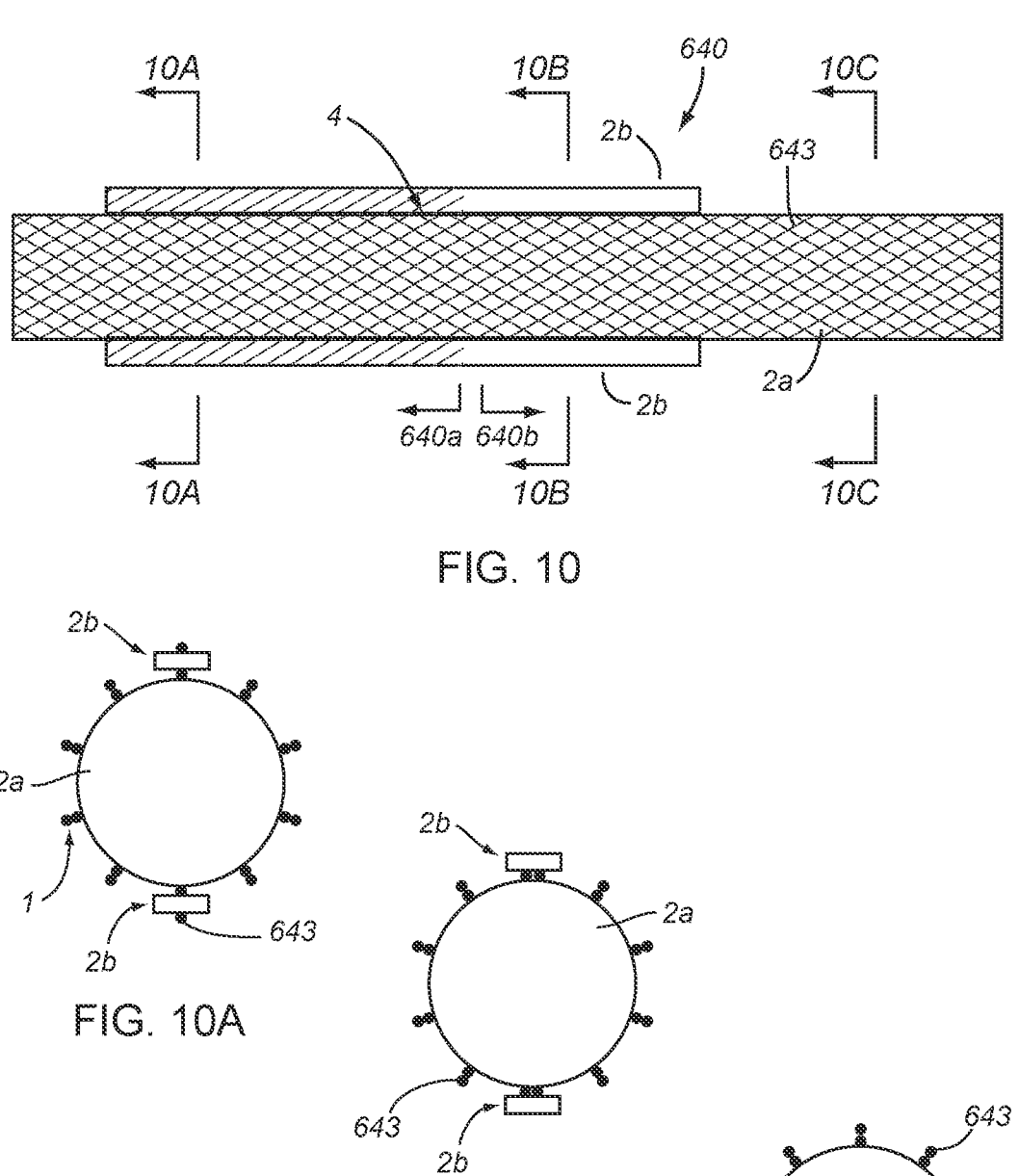
FIG. 10 is a side view of a mandrel/reinforcement subassembly including a pair of secondary mandrels partially braided into a length of the subassembly.
FIGS. 10A-10C are cross-sectional views of the subassembly of FIG. 10 taken along sections 10A-10A, 10B-10B, and 10C-10C, respectively.
Figures 11A, 11B, 11C:
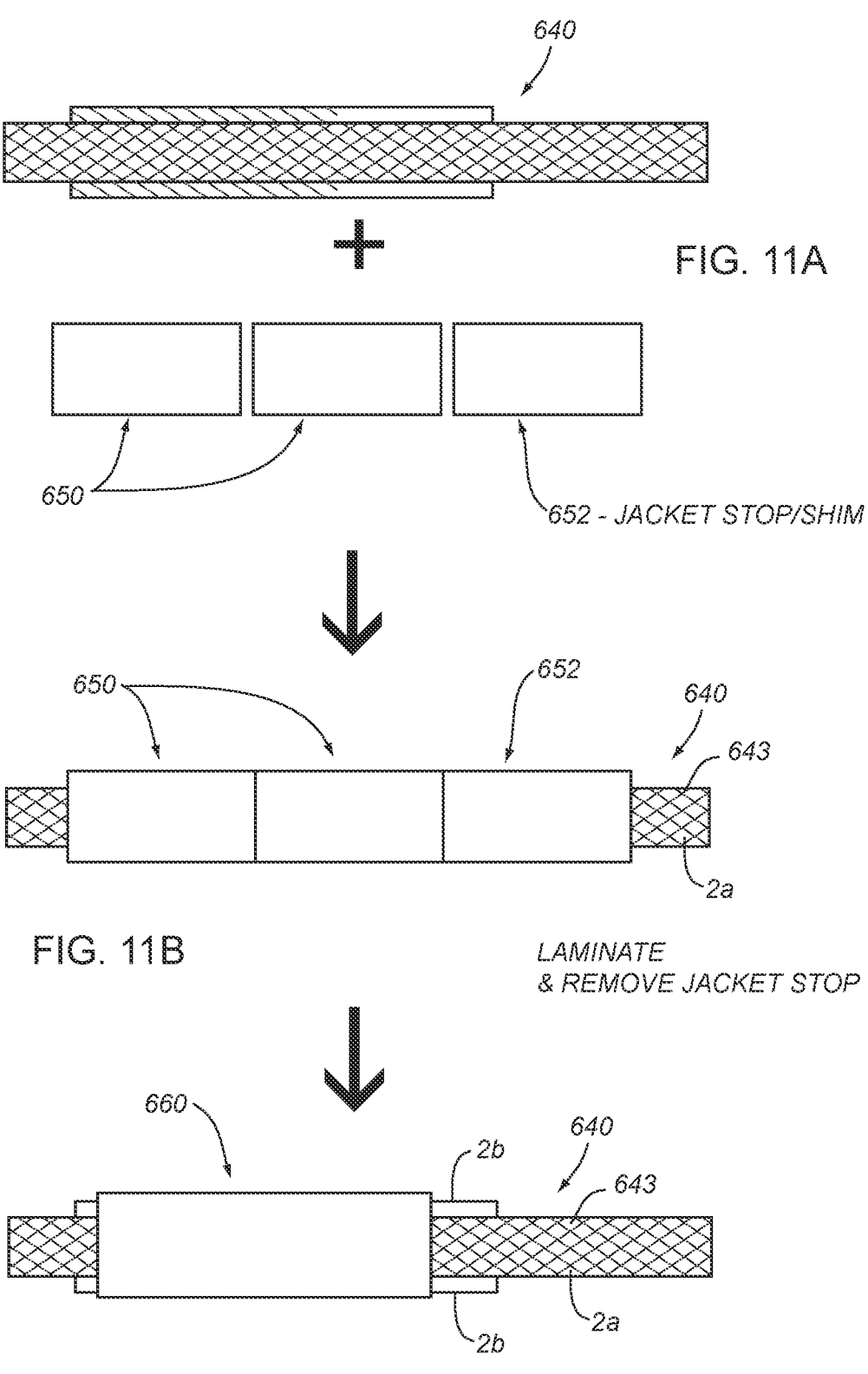
Figures 11H, 11I, 11J:
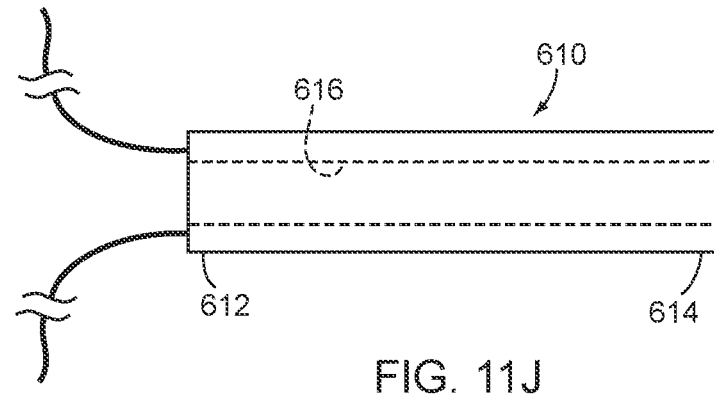

Turning to FIGS. 10-11J, an exemplary method for making a steerable catheter 610 (best seen in FIG. 11J) that generally includes a proximal end 612, a distal end 614, and one or more lumens 616 extending therebetween, similar to other embodiments herein. For example, as shown in FIG. 11J, the catheter 610 includes a central or primary lumen 616*a* and a pair of steering lumens 616*b* slidably receiving respective pull wires 636 coupled to a pull wire ring 638 adjacent the distal end 614. The catheter 610 may be fabricated using similar materials and methods to the previous embodiments, e.g., using a braiding apparatus, similar to that shown in FIGS. 4A and 4B.

For example, turning to FIG. 10, a mandrel/reinforcement subassembly 640 may be made by braiding a plurality of reinforcement members 643 around a primary mandrel 2*a* and at least partially around a pair of secondary mandrels 2*b*, e.g., with the location of the secondary mandrels 2*b* being changed in a predetermined manner along the length of the subassembly 640. In the exemplary embodiment shown, along a first portion 640*a* of the subassembly 640, e.g., corresponding to an intermediate and/or proximal portion of the catheter 610, the secondary mandrels 2*b* are braided into the reinforcement members 643, e.g., such that some of the members 643 are disposed between the primary and secondary mandrels 2*a*, 2*b*, and some members surround both the primary and secondary mandrels 2*a*, 2*b*, as shown in FIG. 10A.

At a second portion 640*b*, e.g., corresponding to a distal portion of the catheter 610, the secondary mandrels 2*b* transition such all of the reinforcement members 643 are braided around only the primary mandrel 2*a*, as shown in FIG. 10B. Braiding of the reinforcement members 643 may continue beyond the ends of the secondary mandrels 2*b*, e.g., as shown in FIG. 10C.

One or more outer layers may then be applied around the subassembly 640 to provide the final catheter 610. For example, as shown in FIG. 11A, a plurality of tubular jackets 650 may be applied around the subassembly 640, e.g., having different materials and/or mechanical properties, as desired for the different portions of the catheter 610. The jackets 650 may be sized to have the subassembly 640 inserted into them such that they abut or are otherwise disposed adjacent one another around the subassembly 640. In addition, a tubular jacket and/or shim 652 (where at least the outer part of the shim 652 is ultimately removable) may be positioned around the subassembly 640, e.g., around the portion 640*b* such that the shim 652 at least partially covers the unconstrained ends of the secondary mandrels 2*b*.

Subsequently, the resulting assembly 660 may be reflowed, heated, and/or otherwise laminated, e.g., similar to other embodiments described elsewhere herein. The shim 652 may then be removed, as shown in FIG. 11C, and then the mandrels 2*b* may also be removed, as shown in FIGS. 11D and 11E. As shown in FIG. 11E, a shoulder 664 (at the right of the assembly 660) remains at the junction between the tubular jackets 650 and the removed shim 652 with the lumens 616*b* created by removal of the secondary mandrels 2*b* exiting from the face of the shoulder 664 in a position radially outward from the reinforcement members 643 present in the portion 640*b*.

Turning to FIG. 11F, a pull wire ring 638 having pull wires 636 extending from its proximal edge may then be inserted over the portion 640*b* with the pull wires 636 may be loaded into the lumens 616*b*. For example, distal ends 636*b* of the pull wires 636 may be attached to the proximal edge of the ring 638, e.g., by welding, soldering, bonding with adhesive, and the like before the ring 638 is inserted over the portion 640*b*. This allows the pull wires 636 to be inserted into the auxiliary lumens 616*b* (not shown in FIG. 11F; see, e.g., FIG. 11E) without taking a substantial bend and the pull wire ring 638 may abut the shoulder 664.

As shown in FIG. 11G, the reinforcement members 643 may then be trimmed at or near the distal edge of the pull wire ring 638 with the pull wire ring constraining the reinforcement members 643 such that, as shown in FIG. 11I, a subsequent a jacket and or tip may be bonded, laminated, reflowed or otherwise attached over and/or beyond the pull wire ring 638 without risk of the reinforcement members 643 rising to or protruding through the surface. Using this method, tip defects may be minimized, stress on the pull wire may be minimized, and/or the assembly may be otherwise considerably improved.

Optionally, the pull wire ring 638 may include one or more features (e.g., holes, slots, etc. not shown) to enhance attachment to the catheter shaft, tip, etc. In addition or alternatively, a thermoplastic liner (e.g., with a coating, similar to other embodiments herein) may be provided on the distal end to enable discrete tip sections to be added and subsequently laminated creating a highly manufacturable device with a completely contiguous/welded liner surface with no edges, discontinuities, or potential for delamination, skiving, leakage, and the like.

Configuring the ring 638 and/or tip jacket components in this manner may provide one or more advantages. For example, lapping the braid or reinforcement layer into and through the ring 638 may eliminate a common kink point that may be a limitation with current devices. In addition, this configuration may eliminate problems with cut end wire protrusions as they are full constrained within the ring 638. In addition, this configuration may provide locations for pull wire lumens that substantially align with desired positions of pull wires, which may case assembly, enhance integrity of the tip, and/or improve alignment of pull forces.

With reference to the previous embodiments, it will be appreciated that lumens and/or mandrels used to create them as described may be replaced by wires, conductors, optical fibers, axial reinforcing elements, e.g., aramid fibers, UHMWPE, or other axial elements. in order to incorporate such elements into the catheter construction for the purpose achieving desired mechanical or functional performance.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A tubular device for a catheter or, the tubular device comprising:

a proximal end and a distal end sized for introduction into a patient's body;

a central lumen extending between the proximal end and the distal end;

an auxiliary lumen extending at least partially between the proximal end and the distal end adjacent the central lumen;

an elongate member received within the auxiliary lumen;

one or more reinforcement members comprising windings extending helically around the central lumen at least partially between the proximal end and the distal end; and one or more layers surrounding the one or more reinforcement members, wherein the tubular device comprises a first portion in which at least some of the windings pass between the central lumen and the elongate member and at least some of the windings surround both the central lumen and the elongate member, and a second portion in which either a) all of the windings surround both the central lumen and the elongate member or b) all of the windings surround the central lumen and the elongate member is disposed outside the windings.

2. The tubular device of claim 1, further comprising one or more additional auxiliary lumens.

3. The tubular device of claim 2, wherein the tubular member includes a pair of auxiliary lumens provided on opposite sides of the central lumen, each auxiliary lumen including an elongate member therein.

4. The tubular device of claim 3, wherein the pair of auxiliary lumens are offset about one hundred eighty degrees (180°) around the circumference of the tubular member.

5. The tubular device of claim 1, wherein, along the second portion, all of the windings surround both the central lumen and the elongate member.

6. The tubular device of claim 5, wherein the tubular device further comprises a third portion adjacent the first portion in which a) at least some of the windings pass between the central lumen and the elongate member and at least some of the windings surround both the central lumen and the elongate member, or b) all of the windings surround the central lumen and the elongate member is disposed outside the windings.

7. The tubular device of claim 1, wherein, along the second portion, all of the windings surround the central lumen and the elongate member is disposed outside the windings.

8. The tubular device of claim 7, wherein the tubular device further comprises a third portion adjacent the first portion in which a) at least some of the windings pass between the central lumen and the elongate member and at least some of the windings surround both the central lumen and the elongate member, or b) all of the windings surround the central lumen and the elongate member is disposed outside the windings.

9. The tubular device of claim 1, wherein the central lumen is substantially aligned around a central longitudinal axis extending between the proximal end and the distal end, and wherein the auxiliary lumen is offset radially from the central axis.

10. The tubular device of claim 1, wherein the elongate member comprises a steering element and wherein the steering element is coupled to the distal end, the steering element configured to apply an axial force to a distal portion of the tubular device and thereby generate a bending moment to bend the distal portion.

11. The tubular device of claim 1, wherein the elongate member comprises a steering element, the tubular device further comprising a pull wire ring adjacent the distal end and wherein a distal end of the steering element is coupled to the pull wire ring.

12. The tubular device of claim 11, wherein the reinforcement members are braided around only the central lumen at a distal portion of the tubular member.

13. The tubular device of claim 11, wherein the reinforcement members terminate at or near a distal edge of the pull wire ring with the pull wire ring constraining the reinforcement members and a jacket and/or tip is bonded, laminated, reflowed or otherwise attached over beyond the pull wire ring.

14. The tubular device of claim 1, wherein the elongate member comprises an elongate conductor.

15. The tubular device of claim 14, further comprising one or more sensors or electrodes on a distal portion of the tubular member adjacent the distal end, the conductor coupled to the one or more sensors or electrodes.

16. The tubular device of claim 15, wherein the distal portion comprises the first portion of the tubular device.

17. The tubular device of claim 16, wherein the conductor comprises one or more segments that transition outside the reinforcement layer, the one or more segments coupled to the one or more sensors or electrodes.

18. The tubular device of claim 14, further comprising a plurality of electrodes spaced apart on a distal portion of the tubular member adjacent the distal end, the conductor coupled to the plurality of electrodes.

19. The tubular device of claim 18, wherein the distal portion comprises the first portion of the tubular device.

20. The tubular member of claim 1, wherein the elongate member comprises a steering element slidably received in the auxiliary lumen.

* * * * *